US008795983B2

(12) United States Patent
Hyman et al.

(10) Patent No.: US 8,795,983 B2
(45) Date of Patent: *Aug. 5, 2014

(54) METHODS FOR THE CHARACTERIZATION OF MICROORGANISMS ON SOLID OR SEMI-SOLID MEDIA

(71) Applicants: Jones Hyman, Wake Forest, NC (US); John Walsh, Durham, NC (US); Thurman Thorpe, Durham, NC (US)

(72) Inventors: Jones Hyman, Wake Forest, NC (US); John Walsh, Durham, NC (US); Thurman Thorpe, Durham, NC (US)

(73) Assignee: bioMerieux, Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/959,802

(22) Filed: Aug. 6, 2013

(65) Prior Publication Data
US 2013/0323718 A1 Dec. 5, 2013

Related U.S. Application Data

(63) Continuation of application No. 12/653,527, filed on Dec. 15, 2009.

(60) Provisional application No. 61/122,925, filed on Dec. 16, 2008.

(51) Int. Cl.
C12Q 1/04 (2006.01)

(52) U.S. Cl.
CPC .................................... C12Q 1/04 (2013.01)
USPC ............................................ 435/34; 435/6.1

(58) Field of Classification Search
None
See application file for complete search history.

(56) References Cited

U.S. PATENT DOCUMENTS

| | | | |
|---|---|---|---|
| 4,847,198 A | 7/1989 | Nelson et al. | |
| 4,957,114 A | 9/1990 | Zeng et al. | |
| 5,112,745 A | 5/1992 | Lorr | |
| 5,474,910 A | 12/1995 | Alfano | |
| 5,660,998 A | 8/1997 | Naumann et al. | |
| 5,663,057 A | 9/1997 | Drocourt et al. | |
| 5,891,394 A | 4/1999 | Drocourt et al. | |
| 5,938,617 A | 8/1999 | Vo-Dinh et al. | |
| 6,571,118 B1 | 5/2003 | Utzinger et al. | |
| 6,780,602 B2 | 8/2004 | Powers et al. | |
| 6,834,237 B2 | 12/2004 | Noergaard et al. | |
| 2002/0086289 A1 | 7/2002 | Straus | |
| 2003/0082516 A1 | 5/2003 | Straus | |
| 2003/0138875 A1 | 7/2003 | Powers et al. | |
| 2003/0143580 A1 | 7/2003 | Straus | |
| 2003/0170613 A1 | 9/2003 | Straus | |
| 2004/0021860 A1 | 2/2004 | Gardner et al. | |
| 2004/0197771 A1 | 10/2004 | Powers et al. | |
| 2005/0273267 A1 | 12/2005 | Maione et al. | |
| 2006/0257929 A1 | 11/2006 | Powers et al. | |
| 2007/0111225 A1 | 5/2007 | Lambert et al. | |
| 2007/0175278 A1 | 8/2007 | Puppels et al. | |
| 2008/0297789 A1 | 12/2008 | Stewart et al. | |
| 2009/0066934 A1 | 3/2009 | Gao et al. | |
| 2009/0156943 A1 | 6/2009 | Phillips et al. | |

FOREIGN PATENT DOCUMENTS

| | | |
|---|---|---|
| CN | 85100424 | 10/1985 |
| CN | 1417347 | 5/2003 |
| CN | 1434285 | 8/2003 |
| CN | 1677088 | 10/2005 |
| CN | 101498666 | 8/2009 |
| WO | 0221108 | 3/2002 |
| WO | 03022999 | 3/2003 |
| WO | 2005068647 | 7/2005 |
| WO | 2007019462 | 2/2007 |
| WO | 2007030020 | 3/2007 |
| WO | 2008105893 | 9/2008 |
| WO | 2009011585 | 1/2009 |
| WO | 2009120532 | 10/2009 |

OTHER PUBLICATIONS

Alimova et al.;Native Fluorescence Changes Induced by Bactericidal Agents;IEEE Sensors Journal (2005)vol. 5 No. 4 pp. 704-711.

Ammor MS; Recent Advances in the use of Intrinsic Fluorescence for Bacterial Identification and Characterization;J. Fluoresc (2007) vol. 17 pp. 455-459.

Bhatta et al.; Use of Fluorescence Spectroscopy to Differentiate Yeast and Bacterial Cells; Appl Microbiol Biotechnol (2006) vol. 71 pp. 121-126.

Bronk et al.; Variability of Steady State Bacterial Fluorescence with Respect to Growth Conditions; App. Spectroscopy (1993) vol. 47 No. 4 pp. 436-440.

Choo-Smith et. al; Investigating Microbial (Micro) colony Heterogeneity by Vibrational Spectroscopy; App. Envir. Micro., (2001) vol. 67, No. 4, pp. 1461-1469.

Dalterio et al.; The Steady-State and Decay Characteristics of Primary Fluorescence From Live Bacteria; App. Spectroscopy (1987) vol. 41 No. 2 234-241.

Estes et al.; Reagentless Detection of Microorganisms by Intrinsic Fluorescence; Biosens Bioelectron. (2003) vol. 18 No. 5-6 511-519.

Giana et al.; Rapid Identification of Bacterial Species by Fluorescence Spectroscopy and Classification Through Principal Components Analysis; J. Fluoresc (2003) vol. 13 489-493.

(Continued)

Primary Examiner — Jon P Weber
Assistant Examiner — Robert Yamasaki

(57) ABSTRACT

The present invention relates to methods and systems for scanning, detecting, and monitoring microorganisms on solid or semi-solid media using intrinsic fluorescence (IF) measurements. The methods are further directed to detection, characterization and/or identification of microorganisms on a solid or semi-solid media using intrinsic fluorescence (IF) measurements that are characteristic of said microorganisms.

13 Claims, 10 Drawing Sheets

(56) References Cited

OTHER PUBLICATIONS

Ginell et al.; Fluorescent Spectrophotometry in the Identification of Bacteria; J. Appl. Bact. (1972) 35(1) 29-36.

Huffman et al.; New method for the detection of micro-organisms in blood: application of quantitative interpretation model to aerobic blood cultures; J. Biom. Optics (May/Jun. 2009) 14(3) pp. 034043-1 through 034043-10.

Kruger et al.; Analysis of the substrate specificity of the *Staphylococcus aureus* sortase transpeptidase SrtA; Biochemistry (Feb. 1, 2004) vol. 43 No. 6 pp. 1541-1551 (Feb. 1, 2004).

Leblanc et al.; Monitoring the identity of bacteria using their intrinsic fluorescence; FEMS Microbiology Letters (2002) 211 147-153.

Maquelin et al.; Raman Spectroscopic Method for Identification of Clinically Relevant Microorganisms Growing on Solid Culture Medium; Anal. Chem., (Jan. 2000) vol. 72, pp. 12-19.

Maquelin et al.; Identification of Medically Relevant Microorganisms by Vibrational Spectroscopy; J. Micro. Methods, (Nov. 1, 2002) vol. 51, No. 3, pp. 255-271.

Maquelin et al.; Prospective Study of the Performance of Vibrational Spectroscopies for Rapid Identification of Bacterial and Fungal Pathogens Recovered from Blood Cultures; J. Clin. Micro., (Jan. 1, 2003) vol. 41, No. 1, pp. 324-329.

Maquelin et al.; Rapid Identification of *Candida* Species by Confocal Raman Microspectroscopy; J. Clin. Micro., (Feb. 2002) vol. 40, No. 2, pp. 594-600.

Mason et al.; Taxonomic Identification of Microorganisms by Capture and Intrinsic Fluorescence Detection; Biosens Bioelectron. (2003) vol. 18, No. 5-6, pp. 521-527.

Pau et al.; A Rapid Enzymatic Procedure for "Fingerprinting" Bacteria by Using Pattern Recognition of Two-Dimensional Fluorescence Data; Clin. Chem. (1986) 32/6, pp. 987-991.

Pau et al.; Evaluation of a Forier-Transform-Based Pattern-Recognition Algorithm for Two-Dimensional Fluorescence Data; App. Spectroscopy (1987) vol. 41, No. 3, pp. 496-502.

Rativa et al.; Optical Spectroscopy on in vitro Fungal Diagnosos; Conf Proc IEEE Eng Med Biol Soc. (2008) vol. 1, pp. 4871-4874.

Sage et al.; Rapid Visual Detection of Microorganisms in Blood Culture; J. Clin. Micro., (Jul. 1984) vol. 20. No. 1, pp. 5-8.

Shelly et al.; Identification of Fluorescent *Pseudomonas* Species; Clin. Chem. (1980) 26/8, pp. 1127-1132.

Shelly et al.; Characterization of Bacteria by Mixed-Dye Fluorimetry; Clin. Chem. (1983) 29/2, pp. 290-296.

Sohn et al.; Fluorescence Spectroscopy for Rapid Detection and Characterization of Bacterial Pathogens; App. Spectroscopy (2009) vol. 63, No. 11, pp. 1251-1255.

Sorrell et al.; Bacterial Identification of Otitis Media With Fluorescence Spectroscopy; Lasers in Surgery and Medicine, (1994) vol. 14, pp. 155-163.

Spector et al.; Noninvasive Fluorescent Identification of Bacteria Causing Acute Otitis Media in a Chinchilla Model; Laryngoscope, (2000) vol. 110, pp. 1119-1123.

Warner et al.; Multicomponent Analysis in Clinical Chemistry by Use of Rapid Scanning Fluorescence Spectroscopy; Clin. Chem. (1976) 22/9, pp. 1483-1492.

The Communication Relating to the Results of the Partial International Search Report for PCT/US2009/006545 dated May 10, 2010.

Co-pending U.S. Appl. No. 12/589,929 "Methods for Isolation and Identification of Microorganisms" filed Oct. 30, 2009.

Co-pending U.S. Appl. No. 12/589,952 "Methods for Separation Characterization and/or Identification of Microorganisms using Spectroscopy" filed Oct. 30, 2009.

English language translation of Russian office action for Russian patent application No. 2011123155, dated Sep. 5, 2013.

English language abstract for CN101498666, obtained from espacenet.com, accessed Jan. 3, 2014.

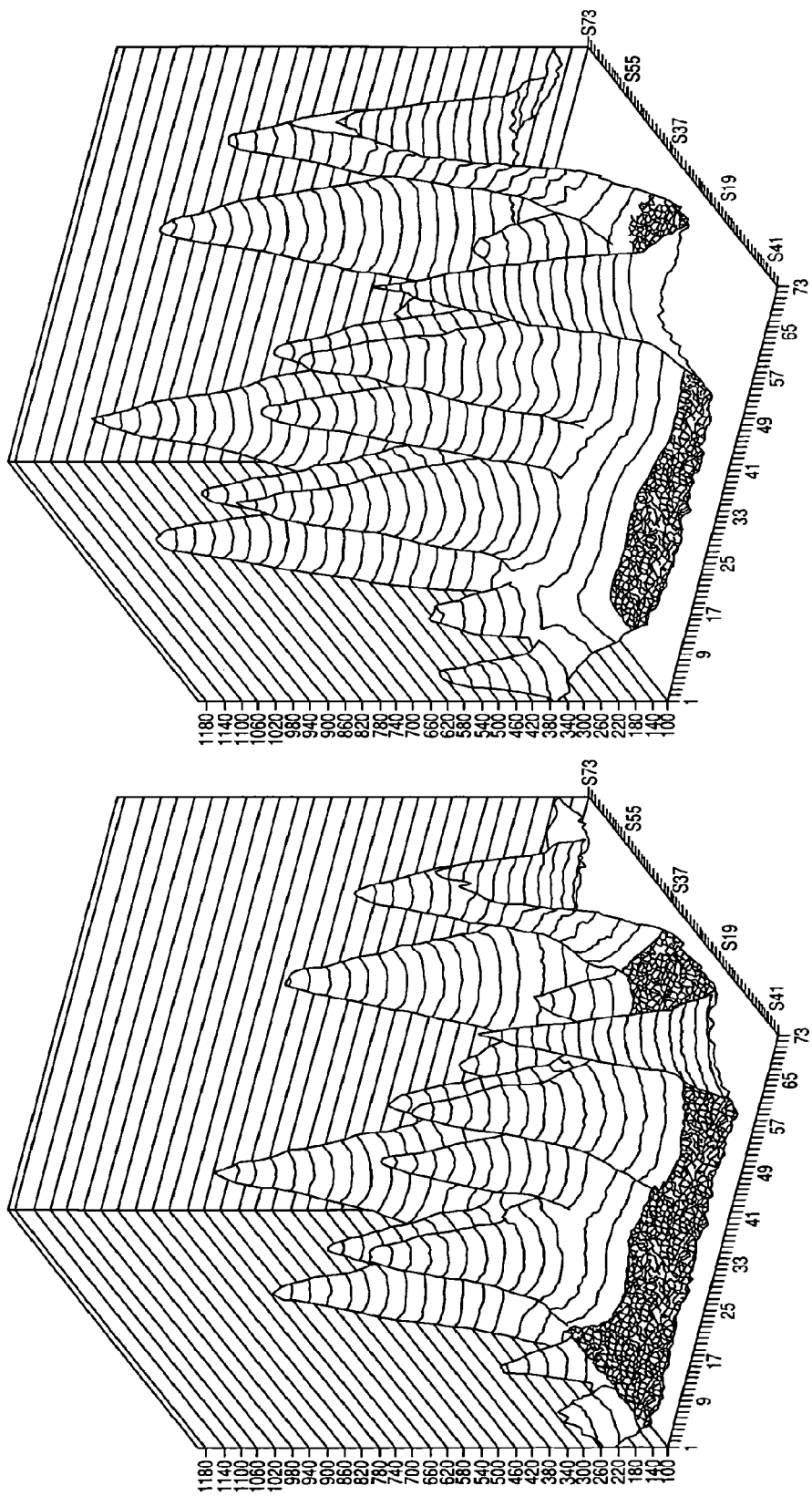

METHODS FOR THE CHARACTERIZATION OF MICROORGANISMS ON SOLID OR SEMI-SOLID MEDIA

CROSS REFERENCE TO RELATED APPLICATIONS

This application is being filed as a continuation of U.S. patent application Ser. No. 12/653,527, which was filed Dec. 15, 2009, is pending, and claims the benefit of U.S. Provisional Patent Application No. 61/122,925, entitled, "Methods for Characterization of Microorganisms on Solid or Semi-Solid Media", filed Dec. 16, 2008.

FIELD OF THE INVENTION

The present invention relates to methods and systems for detecting, monitoring, characterizing, and/or identifying microorganisms on solid or semi-solid media.

BACKGROUND OF THE INVENTION

Microorganisms isolated for the purpose of clinical diagnostics, as well as those isolated to monitor contamination of foodstuffs, medical tissues, or the environment, often need to be characterized in order to determine the appropriate response to the presence of the organisms found. Traditional automated phenotypic identification assays, such as the Vitek®, Phoenix™, and Microscan® systems, or manual phenotypic tests such as API, require that microorganisms be in an appropriate growth phase and free of interfering media and blood products in order to provide robust results. These systems use colonies grown for 16-24 hours on plated media, after which standardized suspensions are made from the colonies, and then the actual characterization tests require a further 4-24 hours of incubation to complete.

Optical spectroscopy methods, such as intrinsic fluorescence (IF), infrared spectroscopy (FTIR), or Raman spectroscopy, have the potential to allow for identification of microorganisms very quickly, but have only been demonstrated to work with "clean" microorganism suspensions. Publications have described IF methods for microbial characterization with only very limited organism sets, or that required additional measures, such as specific binding events, to allow functional characterization. Direct examination of microorganisms on growth medium has been considered problematic due to the assumed large contribution of the medium itself to the spectroscopic pattern.

The present invention overcomes the problems in the art by providing methods that can discriminate between microorganisms spectroscopically interrogated directly on fluorescent solid and/or semi-solid growth media, including highly fluorescent media.

SUMMARY OF THE INVENTION

The present invention provides methods for detecting, monitoring, characterizing, and/or identifying microorganisms on solid and/or semi-solid media. Characterization encompasses the broad categorization or classification of microorganisms as well as the actual identification of a single species. As used herein "identification" means determining to which family, genus, species, and/or strain a previously unknown microorganism belongs to. For example, identifying a previously unknown microorganism to the family, genus, species, and/or strain level. The methods disclosed herein allow the detection, characterization and/or identification of microorganisms more quickly than prior techniques, resulting in faster diagnoses (e.g., in a subject having or suspected of having an infection) and identification of contaminated materials (e.g., foodstuffs and pharmaceuticals). The steps involved in the methods of the invention can be carried out in a short time frame to produce clinically relevant actionable information. In certain embodiments, fast growing organisms can be detected and identified in just a few hours. Slower growing organisms can be detected and identified more quickly than with prior techniques, providing results in a useful timeframe. The identification/characterization step alone can be carried in a few minutes or less. The methods also permit detecting, monitoring, characterizing, and/or identifying multiple types of microorganisms (e.g., different classes and/or species) simultaneously (e.g., in mixed cultures). Advantageously, in some embodiments, the methods of the invention can be performed in situ without destruction of the colony, thereby preserving the colony for further tests or uses. Additionally, the methods of the invention can be partially or fully automated, thereby reducing the risk of handling infectious materials and/or contaminating the samples.

A first aspect of the invention relates to methods of characterizing and/or identifying a microorganism on a solid or semi-solid medium, comprising:
(a) interrogating one or more colonies on a solid or semi-solid medium to produce intrinsic fluorescence (IF) measurements characteristic of a microorganism in the colony; and
(b) characterizing and/or identifying the microorganism in the colony based on intrinsic fluorescence (IF) measurements.

Another aspect of the invention relates to methods of detecting and characterizing a microorganism on a solid or semi-solid medium, comprising:
(a) scanning a medium, known to contain, or that may contain one or more microorganism colonies to locate said colonies present on the medium;
(b) interrogating one or more colonies located during step (a) to produce intrinsic fluorescence (IF) measurements characteristic of a microorganism in the colony; and
(c) detecting, characterizing and/or identifying the microorganism in the colony based on said intrinsic fluorescence (IF) measurements.

A further aspect of the invention relates to methods of characterizing and/or identifying a microorganism in a sample, comprising:
(a) growing a microorganism present in the sample on a solid or semi-solid medium to produce at least one colony;
(b) interrogating one or more colonies on the medium to produce intrinsic fluorescence (IF) measurements characteristic of the microorganism; and
(c) characterizing and/or identifying the microorganism in the colony based on the produced measurements.

An additional aspect of the invention relates to methods of detecting the presence of a microorganism in a sample, comprising:
(a) obtaining a sample known to contain or that may contain a microorganism;
(b) growing a microorganism present in the sample on a solid or semi-solid medium; and
(c) locating any colonies present on the medium by conducting a point-by-point scanning of said solid or semi-solid medium to produce intrinsic fluorescence (IF) measurements; wherein the presence of one or more colonies as located by the produced measurements indicates that a microorganism is present in the sample.

In one embodiment, the invention relates to a system for detecting, characterizing and/or identifying a microorganism on a solid or semi-solid medium, the system comprising a spectrophotometer and focusing optics, such as a lens system or a microscope. In other embodiments, the system further comprises a mechanism for scanning the surface of the medium and/or a mechanism for controlling the environment of (e.g., incubating) the medium.

In another embodiment, a colony can be interrogated to produce measurements which can be used to detect, characterize and/or identify the microorganisms of the colony (e.g., the colony can be interrogated using spectroscopy). The microorganisms can be characterized and/or identified by comparing the measurements (e.g., the spectrum) of the colony to similar measurements (e.g., spectrum or spectra) taken of known microorganisms. In another embodiment, the colony can be interrogated non-invasively (e.g., within a sealed plate). The ability to characterize and/or identify the microorganisms contained in a colony directly (e.g., within a sealed plate) without further handling enhances the safety of microbial identification.

In yet another embodiment, the spectroscopic interrogation is based on intrinsic characteristics of the microorganisms (e.g., intrinsic fluorescence). In other embodiments, the spectroscopic interrogation is based in part on signals obtained from additional agents that are added during the methods of the invention and interact with specific microorganisms or groups of microorganisms.

In another embodiment, the methods further comprise a step of recovering the colony, resuspending the colony and performing further identification and/or characterization tests (e.g., drug resistance, virulence factors, antibiogram).

The present invention is explained in greater detail in the figures herein and the description set forth below.

BRIEF DESCRIPTION OF THE FIGURES

FIGS. 4A-4F show three dimensional plots of the point-by-point IF search scans of run F, where height equals fluorescence intensity. The plots show measurements taken at 6 h (A), 8 h (B), 10 h (C), 12 h (D), 16 h (E), and 24 h (F).

DETAILED DESCRIPTION OF THE INVENTION

Figure 1A:
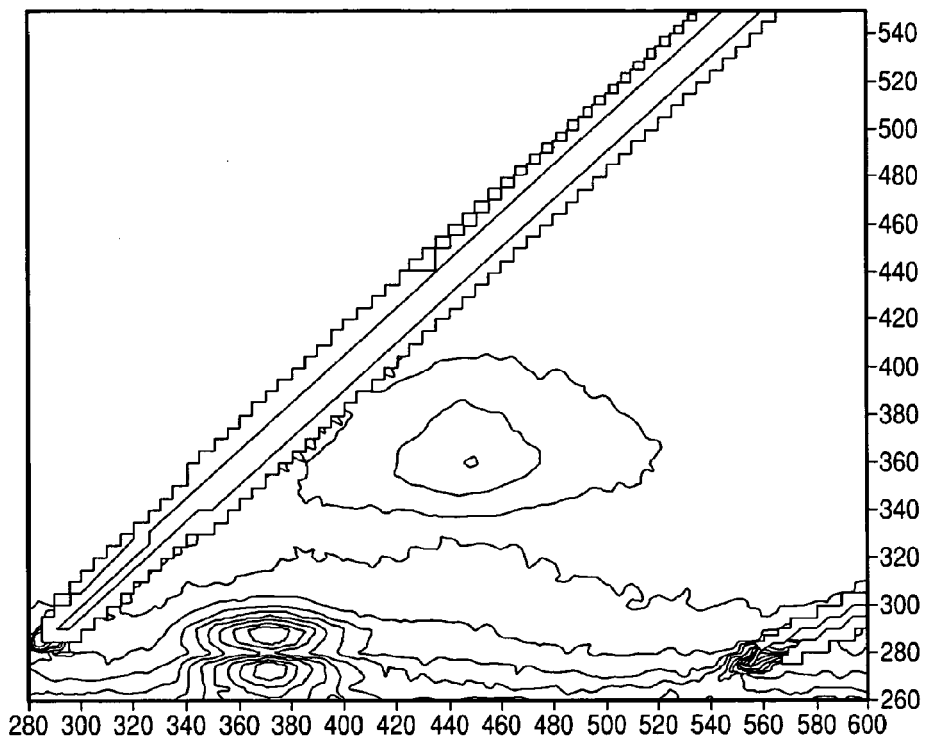
FIGS. 1A-1D show spectra from uninoculated blood agar plates (BAP) with no membrane (A) or BAP with Pall Metricel Black gridded polyethersulfone membrane (Pall) (B), Whatman black mixed ester membrane (WME) (C), or Whatman track-etched polycarbonate black membrane (WPC) (D) laid across the surface of the medium.
Figure 1B:
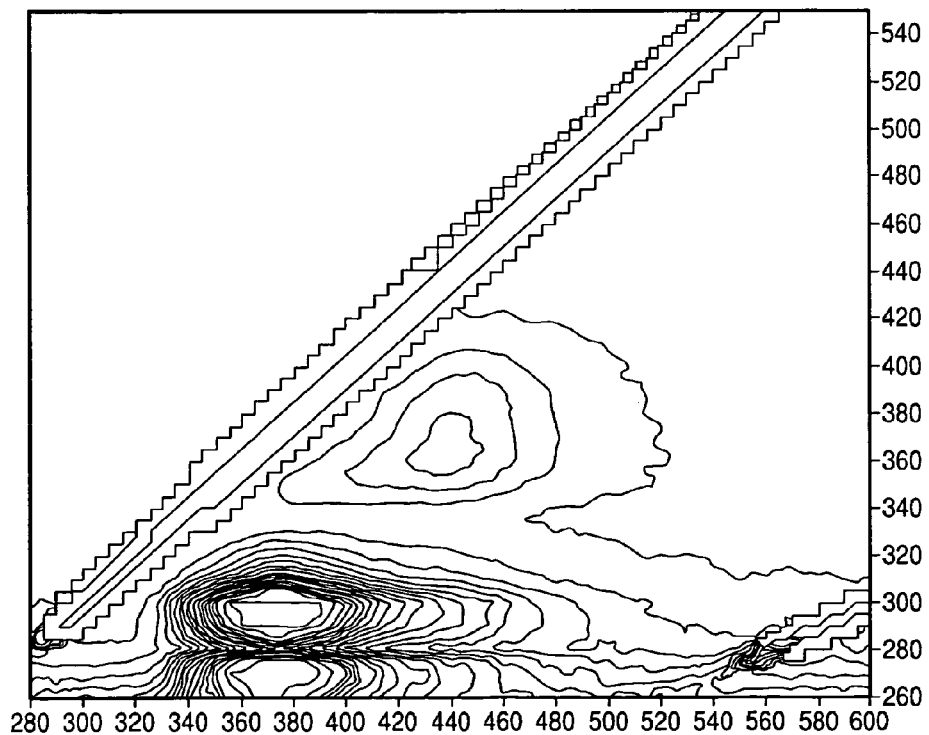
Figure 1C:
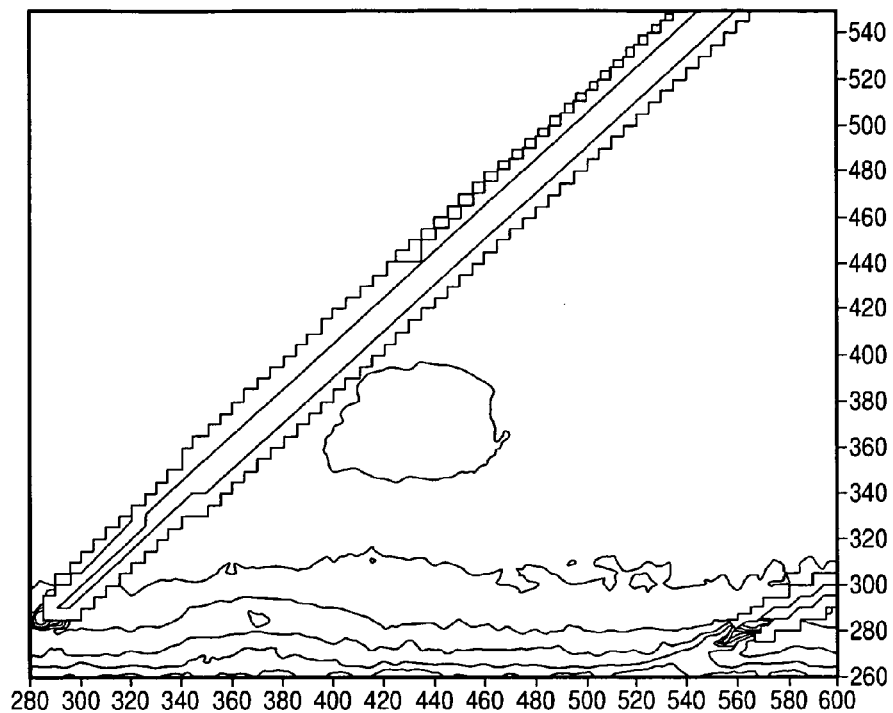
Figure 1D:
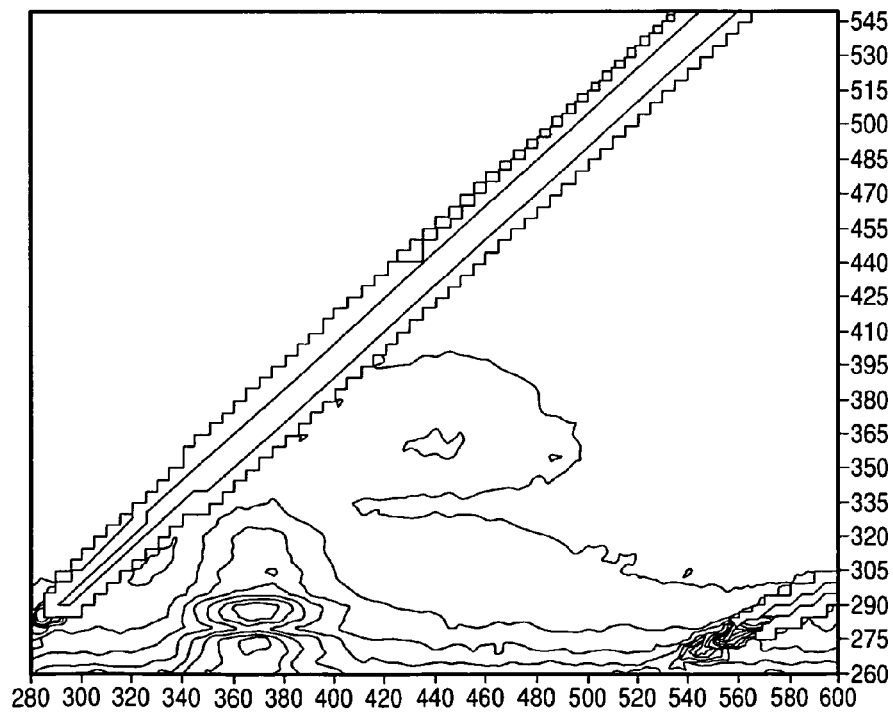

The present invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

DEFINITIONS

As used herein, "a," "an," or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent, dose, time, temperature, and the like, is meant to encompass variations of ±20%, ±10%, ±5%, ±1%, ±0.5%, or even ±0.1% of the specified amount.

As used herein, the term "microorganism" is intended to encompass organisms that are generally unicellular, which can be multiplied and handled in the laboratory, including but not limited to, Gram-positive or Gram-negative bacteria, yeasts, molds, parasites, and mollicutes. Non-limiting examples of Gram-negative bacteria of this invention include bacteria of the following genera: *Pseudomonas, Escherichia, Salmonella, Shigella, Enterobacter, Klebsiella, Serratia, Proteus, Campylobacter, Haemophilus, Morganella, Vibrio, Yersinia, Acinetobacter, Stenotrophomonas, Brevundimonas, Ralstonia, Achromobacter, Fusobacterium, Prevotella, Branhamella, Neisseria, Burkholderia, Citrobacter, Hafnia, Edwardsiella, Aeromonas, Moraxella, Brucella, Pasteurella, Providencia*, and *Legionella*. Non-limiting examples of Gram-positive bacteria of this invention include bacteria of the following genera: *Enterococcus, Streptococcus, Staphylococcus, Bacillus, Paenibacillus, Lactobacillus, Listeria, Peptostreptococcus, Propionibacterium, Clostridium, Bacteroides, Gardnerella, Kocuria, Lactococcus, Leuconostoc, Micrococcus, Mycobacteria* and *Corynebacteria*. Non-limiting examples of yeasts and molds of this invention include those of the following genera: *Candida, Cryptococcus, Nocardia, Penicillium, Alternaria, Rhodotorula, Aspergillus, Fusarium, Saccharomyces* and *Trichosporon*. Non-limiting examples of parasites of this invention include those of the following genera: *Trypanosoma, Babesia, Leishmania, Plasmodium, Wucheria, Brugia, Onchocerca*, and *Naegleria*. Non-limiting examples of mollicutes of this invention include those of the following genera: *Mycoplasma* and *Ureaplasma*.

As used herein, the terms "colony" and "microcolony" refer to a multiplicity or population of microorganisms that lie in close proximity to each other, that lie on a surface, and that are the clonal descendants, by in situ replication, of a single ancestral microorganism. In general, a "colony" is visible to the human eye and is typically greater than about 50 µm, 60 µm, 80 µm, or 100 µm, in diameter. However, as used herein, unless otherwise stated, the term "colony" is meant to include both colonies having a diameter of 50 µm or more, and "microcolonies" having a diameter of 50 µm or less. In other embodiments, the present invention is directed to scanning, detecting, characterizing and/or identifying microorganisms in a "microcolony." As used herein, a "microcolony" can range from about 2 μm to about 50 μm or from about 10 μm to about 50 μm. A "microcolony" is generally too small to be visible to the naked eye (e.g., less than about 50 μm in diameter).

As used herein, the terms "scan" or "scanning" refer to searching a predefined area in a systematic or predetermined pattern, or randomly, to locate something of interest (e.g., a microorganism colony). For example, a solid or semi-solid medium can be "scanned" by moving a focused beam of light in a systematic or predetermined pattern, or randomly, over a surface in order to detect, locate or otherwise sense a microorganism colony. In an alternative embodiment, the solid or semi-solid medium can be moved in a systematic or predetermined pattern, or randomly, relative to the light beam to detect, locate or otherwise sense a microorganism colony. In accordance with this embodiment, the light source typically has a beam diameter of less than about 0.5 mm, less than about 0.2 mm, or less than 0.1 mm. In another embodiment, the beam diameter is from about 5 μm to about 500 μm, from about 10 μm to about 100 μm, or from about 20 μm to about 80 μm.

In one embodiment, the "scanning" may comprises a point-by-point "scan" of the solid or semi-solid medium. In accordance with this embodiment a light source (e.g., a laser beam) can be moved to a first point on the solid or semi-solid medium and a scanning or interrogation step carried out for the detection and/or characterization of any microorganism colonies that may be present. Alternatively, the solid or semi-solid medium can be moved relative to the light source such that a point-by-point scanning is conducted of the solid or semi-solid medium. Subsequently, the light source (e.g., a laser beam), or the solid or semi-solid medium, can be moved such that a second point on the medium can be scanned and/or interrogated. This point-by-point scanning process can be continued until a point-by-point search of a given search area is completed. The search area can be the entire surface of the solid or semi-solid medium (e.g., a medium plate) or a subset thereof.

In another embodiment, the point-by-point search can be carried out from point-to-point along a linear trajectory (e.g., a long a straight line across the medium). Subsequently, the light source, or medium, can be shifted to a second linear line, and a point-by-point search conducted along the linear trajectory of the second linear line. This point-by-point and line-by-line search pattern (or grid type scan) can be continue until a given search area is completed. The search area can be the entire surface of the solid or semi-solid medium (e.g., a medium plate) or a subset thereof. In another embodiment, the scan be a continuous scanning (i.e., a continuous point-by-point scanning).

The present invention provides methods for detecting, monitoring, characterizing, and/or identifying microorganisms on a solid or semi-solid medium. The rapid methods allow the detection, characterization and/or identification of microorganisms more quickly than prior techniques, resulting in faster diagnoses (e.g., in a subject having or suspected of having an infection), characterization and/or identification of contaminated materials (e.g., foodstuffs, water supplies, and pharmaceuticals). The steps involved in the methods of the invention, from obtaining a sample to characterization/identification of microorganisms, can be carried out in a short time frame to obtain clinically relevant actionable information. In certain embodiments, the methods of the invention can be carried out in less than about 72 hours, e.g., in less than about 18, 12, 10, 9, 8, 7, 6, 5, 4, 3, 2, or 1 hour. In certain embodiments, the identification steps can be carried out in less than 60 minutes, e.g., less than about 50, 40, 30, 20, 10, 5, 4, 3, 2, or 1 minute. The methods can be used to characterize and/or identify any microorganism as described herein. In one embodiment, the microorganism is a bacterium. In another embodiment, the microorganism is a yeast. In another embodiment, the microorganism is a mold. The methods can be used to detect, monitor, characterize, and/or identify multiple types of microorganisms, e.g., microorganisms of different species, genuses, families, orders, classes, phyla, and/or kingdoms. In one embodiment, the methods of the invention permit the characterization and/or identification of some or all of the different types of microorganisms present in a sample, e.g., in a mixed culture. In other embodiments, the methods can be used to characterize and/or identify two or more different types of bacteria, two or more different types of yeast, two or more different types of mold, or two or more different types of a mixture of bacteria, yeast, and or mold. The detection of each of the multiple types of microorganisms can occur simultaneously or nearly simultaneously. Additionally, the methods of the invention can be partially or fully automated, thereby reducing the risk of handling infectious materials and/or contaminating the samples.

A first aspect of the invention relates to methods of characterizing and/or identifying a microorganism on a solid or semi-solid medium, comprising:
(a) interrogating one or more colonies on a medium to produce intrinsic fluorescence (IF) measurements characteristic of a microorganism in the colony; and
(b) characterizing and/or identifying the microorganism in the colony based on the produced measurements.

Another aspect of the invention relates to methods of detecting, characterizing and/or identifying a microorganism on a solid or semi-solid medium, comprising:
(a) scanning a medium known to contain, or that may contain one or more microorganism colonies to locate said colonies present on the medium;
(b) interrogating one or more colonies located during step (a) to produce intrinsic fluorescence (IF) measurements characteristic of a microorganism in the colony; and
(c) characterizing and/or identifying the microorganism in the colony based on the produced measurements.

A further aspect of the invention relates to methods of characterizing and/or identifying a microorganism in a sample, comprising:
(a) growing a microorganism present in the sample on a solid or semi-solid medium to produce at least one colony;
(b) interrogating one or more colonies on the medium to produce intrinsic fluorescence (IF) measurements characteristic of the microorganism; and
(c) characterizing and/or identifying the microorganism in the colony based on the produced measurements.

An additional aspect of the invention relates to methods of detecting the presence of a microorganism in a sample, comprising:
(a) obtaining a sample known to contain or that may contain a microorganism;
(b) growing a microorganism present in the sample on a solid or semi-solid medium; and
(c) locating any colonies present on the medium by scanning the medium to produce intrinsic fluorescence (IF) measurements;
wherein the presence of one or more colonies as located by the produced measurements indicates that a microorganism is present in the sample.

Samples that may be tested by the methods of the invention include both clinical and non-clinical samples in which microorganism presence and/or growth is known or suspected, as well as samples of materials that are routinely or occasionally tested for the presence of microorganisms. The amount of sample utilized may vary greatly due to the versatility and/or sensitivity of the method. Sample preparation can be carried out by any number of techniques known to those skilled in the art.

Clinical samples that may be tested include any type of sample typically tested in clinical and/or research laboratories, including, but not limited to, blood, serum, plasma, blood fractions, joint fluid, urine, semen, saliva, feces, cerebrospinal fluid, gastric contents, vaginal secretions, tissue homogenates, bone marrow aspirates, bone homogenates, sputum, aspirates, swabs and swab rinsates, other body fluids, and the like.

The present invention finds use in research as well as veterinary and medical applications. Suitable subjects from which clinical samples can be obtained are generally mammalian subjects, but can be any animal. The term "mammal" as used herein includes, but is not limited to, humans, non-human primates, cattle, sheep, goats, pigs, horses, cats, dog, rabbits, rodents (e.g., rats or mice), etc. Human subjects include neonates, infants, juveniles, adults and geriatric subjects. Subjects from which samples can be obtained include, without limitation, mammals, birds, reptiles, amphibians, and fish.

Non-clinical samples that may be tested include substances encompassing, but not limited to, foodstuffs, beverages, pharmaceuticals, cosmetics, water (e.g., drinking water, non-potable water, and waste water), seawater ballasts, air, soil, sewage, plant material (e.g., seeds, leaves, stems, roots, flowers, fruit), blood products (e.g., platelets, serum, plasma, white blood cell fractions, etc.), donor organ or tissue samples, biowarfare samples, and the like. The method is also particularly well suited for real-time testing to monitor contamination levels, process control, quality control, and the like in industrial settings.

The volume of the sample should be sufficiently large to produce one or more colonies when plated on medium. Appropriate volumes will depend on the source of the sample and the anticipated level of microorganisms in the sample. For example, a clinical swab from an infected wound will contain a higher level of microorganisms per volume than a drinking water sample to be tested for contamination, so a smaller volume of swab material will be needed as compared to the drinking water sample. In general, the sample size can be at least about 50 ml, e.g., 100 ml, 500 ml, 1000 ml or more. In other embodiments, the sample can be less than about 50 ml, e.g., less than about 40 ml, 30 ml, 20 ml, 15 ml, 10 ml, 5 ml, 4 ml, 3 ml, or 2 ml. In certain embodiments, the sample size can be about 1 ml or less, e.g., about 750 µl, 500 µl, 250 µl, 100 µl, 50 µl, 25 µl, 10 µl, 5 µl, 1 µl, 0.5 µl, 0.1 µl, or less. For embodiments in which the sample size is large, the sample can be filtered (e.g., through a filter membrane) and/or concentrated via methods well known in the art (e.g., centrifugation, evaporation, etc.) to reduce the volume and/or collect any microorganisms in the sample. Microorganisms collected on a filter membrane can be resuspended and placed on solid or semi-solid media or the filter membrane can be placed directly on semi-solid media.

Samples to be tested are placed on a suitable medium and incubated under conditions that are conducive to growth of microorganisms. The medium can be selected based on the type(s) of microorganisms known to be or suspected to be in the sample. Appropriate growth media for different microorganisms are well known to those of skill in the art. The growth media can be any medium that provides appropriate nutrients and restricts movement of the microorganisms (i.e., provides localized growth). In some embodiments, the medium can be a semi-solid medium, such as agar, gelatin, alginate, carrageenan, or pectin. Suitable media include media having different functions that are well known to those of skill in the art, including without limitation general purpose media, selective media, differential media, and/or chromogenic media. Media can be selected and/or adjusted such that meaningful measurements (e.g., IF measurements) can be obtained. Examples of suitable semi-solid media include, without limitation, A C agar, Acetobacter agar, Acriflavine-ceftazidime agar, Actinomyces agar, Actinomycete isolation agar, Aeromonas isolation agar, Anaerobic agar, Anaerobic blood agar, Anaerobic TVLS agar, APT agar, Ashby's mannitol agar, Aspergillus differentiation agar, ASS agar, Aureus agar, Azide blood agar, B.T.B. lactose agar, Bacillus agar, Baird Parker agar, BiGGY agar, Bile esculin agar, Bile esculin azide agar, Bile salts brilliant green starch agar, Bismuth sulfite agar, Blood agar, Blood agar SLMB, BPL agar, Brain heart infusion agar, Brewer agar, Brilliant green agar, Brilliant green bile agar, Brilliant green phenol red lactose sucrose agar, BROLACIN agar, BROLACIN MUG agar, Brucella agar, BSM agar, Buffered charcoal yeast extract agar, Calcium caseinate agar, Campylobacter selective agar, Candida ident agar, Casein yeast magnesium agar, CASO agar, CATC agar, Cereus selective agar, Cetrimide agar, Chapman Stone agar, China blue lactose agar, Chlamydospore agar, Christensen citrate agar, Christensen's urea agar, Citrate agar, CLED agar, Clostridium agar, Clostridium difficile agar, Coliform agar, Columbia agar, Columbia blood agar, Corn meal agar, Corn meal peptone yeast agar, CPC-agar, Cramp agar, Czapek dox agar, D.T.M. agar, Davis Minimal agar, DCLS agar, Deoxycholate citrate agar, Deoxyribonuclease test agar, DEV ENDO agar, DEV gelatin agar, DEV nutrient agar, Dextrose caseinpeptone agar, Dextrose starch agar, DHL agar, Dichloran rose bengal agar, Diphtheria virulence agar, DNase test agar with toluidine, *E. coli* agar, *E. coli* O157:H7 MUG agar, ECC agar, ECC selective agar, ECD agar, ECD MUG agar, EMB agar, Endo agar, Enterobacter sakazakii agar, *Enterococcus faecium* agar, Enterococcus selective agar, Esculin iron agar, Eugonic agar, Fungal agar, Fungobiotic agar, Gassner agar, Gassner lactose agar, Gelatin iron medium, Gelatin salt agar, Germ count agar, Glucose bromcresol purple agar, GSP agar, Hektoen enteric agar, Kanamycin esculin azide agar, Karmali campylobacter agar, KF-streptococcus agar, King agar, Klebsiella selective agar, Kligler agar, KRANEP agar, Kundrat agar, Lactobacillus bulgaricus agar, Lactose TTC agar, LB agar, Leifson agar, Levine EMB agar, Listeria agar, Listeria mono confirmatory agar, Listeria mono differential agar, Listeria selective agar, Litmus lactose agar, LL agar, LPM agar, LS differential agar, L-top agar, Luria agar, Lysine arginine iron agar, Lysine iron agar, M enterococcus agar, M-17 agar, MacConkey agar, MacConkey agar with crystal violet, sodium chloride and 0.15% bile salts, MacConkey MUG agar, MacConkey-sorbitol agar, Malt agar, Malt extract agar, Mannitol salt phenol red agar, McBride agar, McClung Toabe agar, M-CP agar, Meat liver agar, Membrane filter enterococcus selective agar, Membrane lactose glucuronide agar, M-Endo agar, M-Endo agar LES, MeReSa agar, M-FC agar, Middlebrook 7H10 agar, Middlebrook 7H11 agar, Milk agar, Mitis salivarius agar, MM agar, Modified buffered charcoal agar, MOX agar, MRS agar, MS.O157 agar, M-TEC agar, Mueller Hinton agar, MUG tryptone soya agar, Mycoplasma agar, Noble agar, Nutrient agar, Nutrient gelatin, OF test nutrient agar, OGY agar, OGYE agar, Orange serum agar, Oxford agar, PALCAM listeria selective agar, Pentachloro rose bengal yeast extract agar, Peptone yeast extract agar, Peptonized milk agar, Perfringens agar, Phenol red dextrose agar, Phenol red lactose agar, Phenol red maltose agar, Phenol red sucrose agar, Phenol red tartrate agar, Phenolphthalein phosphate agar, Phenylalanine agar, Plate count agar, Plate count MUG agar, PLET agar, PM indicator agar, Potato dextrose agar, Potato glucose rose bengal agar, Potato glucose sucrose agar, Pril® mannitol agar, Pseudomonas agar, R-2A agar, Raka-Ray agar, Rapid enterococci agar, Reinforced clostridial agar, Rice extract agar, Rogosa agar, Rogosa SL agar, Rose bengal agar, Rose Bengal chloramphenicol agar, S.F.P. agar, Sabouraud 2% glucose agar, Sabouraud 4% glucose agar, Sabouraud dextrose agar, Sabouraud glucose agar with chloramphenicol, Salmonella agar, Salmonella agar according to Oenδz, Salmonella chromogen agar, SD agar, Select agar, Selective agar for pathogenic fungi, SFP agar, S-Gal®/LB agar, Shapton agar, Simmons citrate agar, Skim milk agar, Sorbic acid agar, Spirit blue agar, SPS agar, SS-agar, Standard nutrient agar no. 1, Staphylococcus agar, Streptococcus selective agar, Streptococcus thermophilus isolation agar, Sulfate API agar, Sulfite iron agar, TBX agar, TCBS agar, TCMG agar, Tergitol®-7 agar, Thayer Martin agar, Thermoacidurans agar, Tinsdale agar, Tomato juice agar, Tributyrin agar, Triple sugar iron agar, Tryptic soya agar, Tryptone agar, Tryptone glucose extract agar, Tryptone glucose yeast extract agar, Tryptone soya yeast extract agar, Tryptone yeast extract agar, Tryptose agar, TSC agar, TSN agar, Universal beer agar, UTI agar, Vibrio agar, Vibrio parahaemolyticus sucrose agar, Violet red bile agar, Violet red bile glucose agar, Violet red bile lactose agar, Violet red bile lactose dextrose agar, Vitamin $B_{12}$ culture agar, Vogel-Johnson agar, VRB MUG agar, Wilkins Chalgren anaerobic agar, Wilson Blair agar, WL differential agar, WL nutrient agar, Wort agar, XLD agar, XLT4 agar, Yeast agar, Yeast extract agar, Yeast malt agar, Yeast mannitol agar, Yersinia isolation agar, Yersinia selective agar, YGC agar, YPAD agar, YPDG agar, YPG agar, and YT agar. In one embodiment, the solid or semi-solid medium may further comprise one or more additional additives that enhance or otherwise increase intrinsic fluorescence (IF) measurements of a microorganism colony on the solid or semi-solid medium. Suitable additives for enhancing intrinsic fluorescence may include one or more protein hydrolysates, amino acids, meat and vegetable extracts, carbohydrate sources, buffering agents, resuscitating agents, growth factors, enzyme cofactors, mineral salts, metal supplements, reducing compounds, chelating agents, photosensitizing agents, quenching agents, reducing agents, oxidizing agents, detergents, surfactants, disinfectants, selective agents, metabolic inhibitors, or combinations thereof.

In other embodiments, the medium can be a filter (e.g., a filter membrane or a glass fiber filter), e.g., that is laid on top of a semi-solid medium. In other embodiments, the filter is laid over a material (e.g., an absorbent pad) that has been exposed to (e.g., soaked in) liquid medium. In some embodiments, a sample (e.g., a large volume sample) may be passed through a filter to collect any microorganisms present in the sample. The filter can then be placed on top of growth media and incubated under appropriate conditions for microorganism growth. Suitable filter membranes are well known to those of skill in the art and include any membrane suitable for collecting microorganisms and/or capable of supporting microorganism growth. Examples of membrane materials include, without limitation, cellulose, mixed cellulose ester, nitrocellulose, polyvinylchloride, nylon, polytetrafluoroethylene, polysulfone, polyethersulfone, polycarbonate black, and black mixed ester, including any combination thereof.

The filters can have a pore size suitable for filtering liquids and/or collecting microorganisms, e.g., about 1 to about 25 μm for yeast and about 0.05 μm to about 2 μm, e.g., about 0.2 μm to about 1 μm for bacteria.

In certain embodiments, the medium can be present in a plate, e.g., a standard microbiological agar plate. In some embodiments, the plate can be a multiwell plate, having, e.g., 2, 4, 6, 8, 12, 24, 32, 48, 64, 96, 128, or more wells per plate, for testing of multiple samples. The plate can be made of any suitable material for growing microorganisms, e.g., polystyrene or glass. The plate optionally has a lid. If the interrogation of colonies occurs while the lid is in place, the lid and/or the plate can contain at least one area that is transparent to at least a portion of the ultraviolet, visible light, and/or near infrared spectrum to permit interrogation through the lid and/or plate.

In the methods of the invention, the phrases "growing microorganisms present in the sample on a solid or semi-solid medium" and "a sample is placed on a medium" include any manner of contacting the sample with the medium such that microorganisms present in the sample can grow and produce colonies. In certain embodiments, the sample is placed on the surface of the solid or semi-solid medium. In other embodiments, the sample may be mixed with the medium in a liquid state and than allowed to solidify (e.g., pour plates) such that any colonies that grow are embedded within the medium. In another embodiment, a sample can be mixed with dehydrated medium such that the medium is rehydrated and then allowed to solidify.

In one embodiment, the solid or semi-solid medium is at the bottom of a container containing microorganisms suspended in a liquid above the medium. The container can then be manipulated (e.g., centrifuged) to place the microorganisms on the medium. The liquid can then be removed and the medium incubated for colony growth. For example, a blood sample can be introduced into a blood culture tube containing a liquid growth medium and a solid or semi-solid medium at the bottom. The culture tube is then centrifuged to place the microorganisms on the solid or semi-solid medium (optionally after red blood cells are lysed), the liquid removed, and the microorganisms grown, detected, and/or identified according to the methods of the invention.

Once a sample is placed on a medium (e.g., by spreading a liquid sample on the medium using standard microbiological techniques and/or by placing a filter membrane on a semi-solid medium), the medium is incubated under conditions suitable for growth of microorganisms present in the sample. Appropriate conditions are well known to those of skill in the art and will depend on the microorganisms and the medium. The medium can be incubated at a temperature of about 20° C. to about 50° C., e.g., about 25° C. to about 45° C., e.g., about 37° C. The incubation time is sufficient for detectable colonies to appear (visually or spectroscopically) and will depend on the microorganism(s), the temperature, the medium, the level of nutrients, and other conditions that determine growth rate. In some embodiments, the incubation time can be about 12 hours or less, e.g., about 11, 10, 9, 8, 7, 6, 5, 4, 3, 2, or 1 hour or less. In certain embodiments, such as under slow growing conditions or with slow growing microorganisms (e.g., mycobacteria), the incubation time can be about 12 hours or more, e.g., about 18, 24, 36, 48, or 72 hours or more. In some embodiments, the medium is incubated in an incubator and the medium is removed from the incubator one or more times and placed in an apparatus to detect and/or identify any colonies growing on the medium. In other embodiments, the medium can be incubated directly in the apparatus used to detect and/or identify colonies, e.g., in a temperature-controlled plate holder.

In one aspect, the invention relates to the interrogation of a colony of microorganisms on a solid or semi-solid medium to produce IF measurements which identify the microorganism that makes up the colony. In one embodiment, the interrogation is by fluorescence spectroscopy. The interrogation can take place in a non-invasive manner, that is, the colony can be interrogated while it remains intact on the medium. In another embodiment, the plate containing the medium and the colony remains sealed (e.g., the lid is not removed) throughout the interrogation. In accordance with this embodiment, the plate, or a portion thereof, may be composed of a material that is transparent to light (e.g., at least a portion of the near infrared (NIR; 700 nm-1400 nm), ultraviolet (UV; 190 nm-400 nm) and/or visible (VIS; 400 nm-700 nm) light spectrum). Examples of suitable materials include, without limitation, acrylic, methacrylate, quartz, fused silica, sapphire, a cyclic olefin copolymer (COC) and/or a cyclo olefin polymer (COP) (e.g., Zeonex® (Zeonex®, San Diego, Calif.)). The ability to detect and/or identify the microorganisms in a non-invasive manner, optionally coupled with keeping the plate sealed throughout the identification process, as well as automating some or all of the procedure, decreases the risks from handling microorganisms that are or may be infectious and/or hazardous, as well as the risk of contaminating the sample. Furthermore, the ability to identify microorganisms by direct interrogation without further processing of the pellet (e.g., suspension and replating and/or other identification assays), greatly increases the speed with which identification can be made. In other embodiments, the colony is suspended in a solution and optionally removed from the medium prior to interrogation. In another embodiment, the colony is suspended in a solution after in situ interrogation and further interrogation is then carried out. For example, techniques such as latex agglutination tests or automated phenotypic identification tests that can be applied to isolated microorganisms but not a colony of microorganisms on a medium can be carried out on the suspended microorganisms.

In some embodiments, the spectroscopy can be used to analyze the intrinsic fluorescence properties of the microorganisms, e.g., a property present within the microorganism in the absence of additional agents, such as stains, dyes, binding agents, etc. In other embodiments, in addition to analyzing IF, the spectroscopy can also be used to analyze one or more extrinsic properties of the microorganism(s), e.g., a property that can only be detected with the aid of additional agents. The spectroscopic interrogation can be carried out by any technique known to those of skill in the art to be effective for detecting and/or identifying one or more intrinsic or extrinsic properties of microorganisms. For example, front face fluorescence (where the exciting and emitted light enters and leaves the same optical surface, and if the sample is generally optically thick, the excitation light penetrates a very short distance into the sample (see, e.g., Eisinger, J., and J. Flores, "Front-face fluorometry of liquid samples," *Anal. Biochem.* 94:15 (1983)) can be used for identification of microorganisms in pellets. Other forms of measurement, such as epifluorescence, reflectance, absorbance, and/or scatter measurements, can also be employed in the present invention.

In one aspect of the invention, the spectroscopy is carried out using focusing optics, such as a lens system or a microscope set up to permit observations in the ultraviolet, visible, and infrared range functionally linked to a spectrophotometer (e.g., using fiber optics). In one embodiment, the medium (e.g., in a plate), is placed on a microscope stage where it can be interrogated by an excitation source as well as observed visually (e.g., through the microscope). In one embodiment, the plate can be manually manipulated to position colonies for interrogation, either by moving the plate itself or moving the microscope stage to which the plate is affixed. In another embodiment, the microscope stage is automatically controlled (e.g., a motorized stage) such that a plate affixed to the stage can be scanned (e.g., in a set pattern designed to cover the entire section to be scanned). In another embodiment, the medium held stationary while a focused light beam, such as a laser, is scanned across the medium and the emitted light is detected by an imaging or non-imaging detector. In a further embodiment, the microscope can comprise a plate incubator with a temperature control (e.g., a water bath) so that the plate can remain under the microscope and be interrogated during incubation of the medium.

In one aspect of the invention, an excitation source is directed at a single colony to produce IF measurements. The colony can be any size at the time of interrogation as long as it is sufficiently large for an accurate measurement to be made. In one embodiment, a colony can be interrogated when it is undetectable by the human eye. For example, a colony can be interrogated when the colony comprises less than about 10,000 microorganisms, e.g., less than about 5000, 1000, 500, 400, 300, 200, or 100 microorganisms. In other embodiments, a colony can be interrogated when the colony is less than about 1000 µm in diameter or less than about 1000 µm in length in its longest dimension (if the colony is not round). For example, a colony can be interrogated when the colony is about 900, 800, 700, 600, 500, 400, 300, 200, 100, 50, or 25 µm or less. In one embodiment, the excitation beam is smaller in diameter than the colony to be interrogated, such that the entire beam can be directed at a colony and the medium does not substantially interfere with the IF measurement. In certain embodiments, the excitation beam has a diameter of less than about 1000 µm, e.g., less than about 900, 800, 700, 600, 500, 400, 300, 200, 100, 50, or 25 µm. The size of the excitation beam, as well as the size of the emission beam, can be controlled, e.g., with the use of pinholes. In some embodiments, the excitation beam is directed at the center of the colony. In other embodiments, the excitation beam is directed at other parts of the colony (e.g., at and/or near the edge) where the microorganisms may be in a different growth and/or metabolic state than those at the center of the colony. In a further embodiment, the excitation beam can be directed at a certain depth within the colony, e.g., using confocal microscopy.

The colony illumination source, or excitation source, may be selected from any number of suitable light sources as known to those skilled in the art. Any portion of the electromagnetic spectrum that produces usable data can be used. Light sources capable of emission in the ultraviolet, visible and/or near-infrared spectra, as well as other portions of the electromagnetic spectrum, can be utilized and are known to those skilled in the art. For example, light sources may be continuum lamps such as a deuterium or xenon arc lamp for generation of ultraviolet light and a tungsten halogen lamp for generation of visible/near-infrared excitation. These light sources provide a broad emission range and the spectral bandwidth for specific excitation wavelengths may be reduced using optical interference filters, prisms and/or optical gratings, as are well known in the art.

Alternatively, a plurality of narrowband light sources, such as light emitting diodes and/or lasers, may be spatially multiplexed to provide a multi-wavelength excitation source. For example, light emitting diodes are available from 190 nm to in excess of 900 nm and the sources have a spectral bandwidth of 20-40 nm (full width at half maximum). Lasers are available in discrete wavelengths from the ultraviolet to the near-infrared and can be employed in multiplexing methods well known to those skilled in the art.

The spectral selectivity of any of the light sources may be improved by using spectral discrimination means such as a scanning monochromator. Other methods of discrimination may be utilized, as known to those of skill in the art, such as an acousto-optic tunable filter, liquid crystal tunable filter, an array of optical interference filters, prism spectrograph, etc., and in any combination. A consideration in selecting the spectral discriminator takes into account the range of tunability as well as the level of selectivity. By way of illustration, for example, a discriminator might utilize the wavelength range of 300-800 nm with a selectivity of 10 nm. These parameters generally determine the optimum technology necessary to achieve the tunability range as well as the selectivity.

Typically, the light source results in the excitation of the sample, followed by measurement of the emission of fluorescence from the sample at predetermined time points or continuously. Similarly, the reflected light from interaction of the excitation source with the sample may be measured to provide pertinent data for detection and/or characterization.

The emission from the sample may be measured by any suitable means of spectral discrimination, and in some embodiments employs a spectrometer. The spectrometer may be a scanning monochromator that detects specific emission wavelengths whereby the output from the monochromator is detected by a photomultiplier tube and/or the spectrometer may be configured as an imaging spectrograph whereby the output is detected by an imaging detector array such as a charge-coupled device (CCD) detector array. In one embodiment, a discriminator allows the observation of the fluorescence and/or scattering signal by a photodetection means (such as a photomultiplier tube, avalanche photodiode, CCD detector array, and/or electron multiplying charge coupled device (EMCCD) detector array).

The spectroscopic technique is used to obtain measurements that are preferably provided as Excitation-Emission Matrix (EEM) measurements. As used herein, EEM is defined as the luminescent spectral emission intensity of fluorescent substances as a function of both excitation and emission wavelength, and includes a full spectrum or a subset thereof, where a subset may contain a single or multiple excitation/emission pairs. Additionally, a cross section of the EEM with a fixed excitation wavelength may be used to show the emission spectra for a specific excitation wavelength, and a cross section of the EEM with a fixed emission wavelength may be used to show the excitation spectra for a sample. In one embodiment, multiple EEMs are measured at more than one specific excitation-emission wavelength pair, e.g., at least at 2, 3, 4, 5, 6, 7, 8, 9, 10, 15, 20, 25, 50, or more specific excitation-emission wavelength pairs. In certain embodiments, the number of excitation-emission wavelength pairs measured is sufficient to determine the exact species of the microorganism, e.g., about 5 to about 30 pairs, e.g., about 10 to about 20 wavelength pairs. In other embodiments, the number of excitation-emission wavelength pairs measured is sufficient to at least partially identify the microorganism, e.g., to obtain sufficient useful information for action, e.g., information sufficient to identify a classification group as described below. For example, a suitable number of excitation-emission wavelength pairs to provide useful information for action, such as a classification group, can be about 2 to about 8 pairs, e.g., about 3 to about 5 pairs.

According to the invention, control measurements are taken for colonies of known microorganisms, thus allowing for correlation of measured test data with characterization of the microorganisms of interest using various mathematical methods known to those skilled in the art. For example, the data from samples may be compared with the baseline or control measurements utilizing software systems known to one skilled in the art. More particularly, the data may be analyzed by a number of multivariate analysis methods, such as, for example, General Discriminant Analysis (GDA), Partial Least Squares Discriminant Analysis (PLSDA), Partial Least Squares regression, Principal Component Analysis (PCA), Parallel Factor Analysis (PARAFAC), Neural Network Analysis (NNA) and/or Support Vector Machine (SVM). These methods may be used to classify unknown microorganisms of interest into relevant groups based on existing nomenclature, and/or into naturally occurring groups based on the organism's metabolism, pathogenicity and/or virulence in designing the system for monitoring, detecting and/or characterizing the organism as described previously.

In yet another embodiment, non-spectroscopic measurements from the detection system, such as detection times and growth rates can be used to assist in the characterization and/or identification of microorganisms from the colony. Additionally, measurements taken from a photographic image of the solid or semi-solid media can provide valuable information on the characterization and/or identity of the microorganisms in the colony, such as colony size, shape, color and density.

In some embodiments of the invention, characterization and/or identification of the microorganisms in the colony need not involve identification of an exact species. Characterization encompasses the broad categorization or classification of biological particles as well as the actual identification of a single species. Classification of microorganism from a colony may comprise determination of phenotypic and/or morphologic characteristics for the microorganism. For example, characterization of the biological particles may be accomplished based on observable differences, such as, composition, shape, size, clustering and/or metabolism. In some embodiments, classification of the biological particles of interest may require no prior knowledge of the characteristics of a given biological particle but only requires consistent correlations with empiric measurements thus making this method more general and readily adaptable than methods based on specific binding events or metabolic reactions. As used herein "identification" means determining to which family, genus, species, and/or strain a previously unknown microorganism belongs to. For example, identifying a previously unknown microorganism to the family, genus, species, and/or strain level.

In some instances, characterization encompasses classification models which provide sufficient useful information for action to be taken. As used herein, the preferred classification models comprise grouping into one or more of the following: (1) Gram Groups; (2) Clinical Gram Groups; (3) Therapeutic Groups; (4) Functional Groups; and (5) Natural Intrinsic Fluorescence Groups.

(1) Gram Groups:

Within the Gram Groups classification, microorganisms may be placed into one of three broad classification categories based on their Gram staining reaction and overall size, said groups selected from one or more of the following: (a) Gram positive microorganisms that stain dark blue with Gram staining; (b) Gram negative microorganisms that stain red with Gram staining; and (c) yeast cells that stain dark blue with Gram staining, but are very large rounded cells that are distinguished from bacteria by their morphological characteristics and size.

(2) Clinical Gram Groups:

The Gram Groups may be further divided into several sub-categories representing distinguishing morphological features. These sub-categories comprise all the relevant clinical information reported by an experienced laboratory technologist, and thus provide a higher level of identification than a positive or negative Gram reaction. This particular classification is very helpful because it eliminates concerns about relying on the quality of a Gram stain and/or the skill level of the technician reading the smear by providing the equivalent clinically relevant information with an automated system. More specifically, subcategories of microorganisms based on this classification model may be selected from one or more of the following: (a) cocci, which are small rounded cells; (b) diplococci, which are two small rounded cells joined together; (c) rods, which are rectangular shape; and (d) bacilli, which are rod shaped. Examples of these sub-categories that can be ascertained by additional morphological information include: (i) Gram positive cocci; (ii) Gram positive cocci in chains; (iii) Gram positive cocci in clusters (i.e., "grape-like" clusters); (iv) Gram positive diplococci; (v) Gram positive rods; (vi) Gram positive rods with endospores; (vii) Gram negative rods; (viii) Gram negative coccobacilli; (ix) Gram negative diplococci; (x) yeast; and (xi) filamentous fungi.

(3) Therapeutic Groups:

The therapeutic groups comprise multiple microbial species that, when isolated from particular specimen types, are treated with the same class of antibiotics or mixture of antibiotics (Reference: "*Sanford Guide to Antimicrobial Therapy* 2008"). In many cases, identity to the species level is not required by the clinician to enable a change from initial empiric therapy to a more targeted therapy because more than one species can be treated with the same choice of antibiotic(s). This classification level correctly places these "same-treatment" microorganisms into single therapeutic categories. Examples of this characterization level include the ability to distinguish highly resistant Enterobacteriacae (EB) species from sensitive EB species (*Enterobacter* spp. from *E. coli*), or fluconazole-resistant *Candida* species (*C. glabrata* and *C. kruzei*) from sensitive *Candida* species (*C. albicans* and *C. parapsilosis*), and so on.

(4) Functional Groups:

According to the invention, microorganisms may also be placed into several groups based upon a mixture of metabolic, virulence and/or phenotypic characteristics. Non-fermentative organisms may be clearly distinguished from fermentative ones. Furthermore, microorganism species that produce hemolysins may be grouped separately from non-hemolytic species. In some cases, these groups represent broader categories than genus level (e.g., coliforms, Gram negative non-fermentative rods), some at the genus level (e.g., *Enterococcus, Candida*), and some with closer to species-level discrimination (e.g., coagulase-negative staphylococci, alpha-hemolytic streptococci, beta-hemolytic streptococci, coagulase-positive staphylococci, i.e., *S. aureus*).

(5) Natural Intrinsic Fluorescence ("IF") Groups:

Microorganisms may also be placed into categories based on their natural tendency to group together by their innate and/or intrinsic fluorescence characteristics. Some of these groups may be common to Therapeutic and Functional Group categories. These groupings may comprise individual species, such as *E. faecalis, S. pyogenes,* or *P. aeruginosa* that have characteristic IF signatures and/or may contain small groups of organisms with relatively conserved IF signatures such as the *E. coli-K. oxytoca* or *E. aerogenes* and *C. freundii* groups.

In addition to measuring intrinsic properties of microorganisms (such as intrinsic fluorescence) for identification purposes, the methods of the present invention can further comprise the use of additional identifier agents to aid in the identification process. Agents that bind to specific microorganisms, such as affinity ligands, can be used to separate microorganisms, to identify a class or species of microorganism (e.g., through binding to a unique surface protein or receptor) and/or to identify a characteristic of the microorganism (e.g., antibiotic resistance). Useful identifier agents include, without limitation, monoclonal and polyclonal antibodies and fragments thereof (e.g., anti-Eap for *S. aureus* identification), nucleic acid probes, antibiotics (e.g., penicillin, vancomycin, polymyxin B), aptamers, peptide mimetics, phage-derived binding proteins, lectins, host innate immunity biomarkers (acute phase proteins, LPS-binding protein, CD14, mannose binding lectin, Toll-like receptors), host defense peptides (e.g., defensins, cathelicidins, proteogrins, magainins), bacterocins (e.g., lantibiotics, such as nisin, mersacidin, epidermin, gallidermin, and plantaricin C, and class II peptides), bacteriophages, and fluorescent dyes selective for nucleic acids, lipids, carbohydrates, polysaccharides, capsules/slime or proteins, including any combination. If the agent does not itself give out a detectable signal, the agent can be labeled to provide a detectable signal, such as by conjugating the agent to a marker (e.g., visible or fluorescent). Markers include, without limitation, fluorescent, luminescent, phosphorescent, radioactive, and/or colorimetric compounds. The agent can be added to the microorganisms at any step in the methods of the invention, e.g., when the sample is placed on the medium and/or after colonies have been detected. In some embodiments, the presence and/or amount of the agent in the colony can be determined during interrogation of the colony. Other useful identifier agents include substrates for microbial enzymes, chelating agents, detergents, surfactants, disinfectants (eg. alcohols, bleach, hydrogen peroxide) and toxic compounds (eg. sodium azide, potassium cyanide) and metabolic inhibitors such as cyclohexamide, etc. Similarly, many fluorescent compounds for measuring microbial cell viability, metabolism and/or membrane potential may be used as an identifier agent in the present invention.

In one aspect of the invention, the method can further comprise a step of recovering the microorganism(s) from the colony and performing additional tests. The recovered microorganism(s) can be suspended in a suitable medium, e.g., saline. Once suspended, the microorganism(s) can be subject to any further tests that are desired, as would be known to those of skill in the art and as described above. In particular, any test requiring clean samples of microorganisms can be carried out with the suspended microorganism(s). In some embodiments, additional identification/characterization tests can be performed. Examples of identification tests include Vitek 2, amplified and non-amplified nucleic acid tests (NAT), chromogenic and latex agglutination assays, immunoassays, (e.g., employing labeled primary or secondary antibodies and/or other ligands), mass spectrometry (e.g., MALDI-TOF mass spectrometry) and/or other optical techniques such as infrared spectroscopy (FTIR) or Raman spectroscopy. Additional characterization tests can also be performed, such as drug resistance, antiobiograms, and/or virulence factors. The additional characterization may be part of a test that was started during the initial identification steps of the method. For example, the detection of methicillin resistant *S. aureus* can begin by adding fluorescently-labeled penicillin to the sample prior to growth of colonies. The presence and/or amount of bound penicillin can then be determined, e.g., in the colony or in microorganisms recovered from the colony. In certain embodiments, one or more additional tests can be carried out within the same system in which the identification steps are carried out, e.g., in the same apparatus. In one embodiment, particular additional tests can be selected from a number of available tests based on the identification made.

In one aspect of the invention, some or all of the method steps can be automated. As used herein, the term "automated" means computer controlled. In one embodiment, the various fluorescence emission detection and correlation steps are automated, and the resulting information obtained from the methods is automatically used to populate a database. In further embodiments, other steps in the method, such as detection and/or interrogation of colonies, can also be automated. Automating the steps of the methods not only allows more samples to be tested more quickly, it also reduces the risks of human errors in handling samples that may contain harmful and/or infectious microorganisms and reduces the chances of contaminating the samples and/or exposing the handler to the samples. In one embodiment, the invention relates to a system for detecting and/or identifying a microorganism on a solid or semi-solid medium, the system comprising a spectrophotometer and focusing optics, such as a lens system or a microscope. In other embodiments, the system further comprises a mechanism for scanning the surface of the medium and/or a mechanism for controlling the environment of (e.g., incubating) the medium.

One aspect of the invention relates to the detection of a colony on a solid or semi-solid medium. The detection optionally is followed by identification/characterization of the microorganisms in the colony. In one embodiment, the medium on which a sample has been placed is manually scanned for the presence of colonies. In one embodiment, colonies can be detected visually with the unaided eye. In other embodiments, colonies can be detected using a microscope. For example, the medium can be observed under a microscope while the medium, positioned on the microscope stage, is manually moved under the microscope objective to scan a portion of the medium for the presence of colonies. The medium can be moved by manipulating the medium itself (e.g., moving the plate containing the medium) or moving the microscope stage on which the medium is placed. In other embodiments, the scanning is carried out automatically. In one embodiment, a motorized microscope stage can be programmed to move the medium under the objective in a search pattern across the surface of the medium such that individual portions of the medium can be observed in turn. In another embodiment, the medium held stationary while a focused light beam, such as a laser, is scanned across the medium and the emitted light is detected by an imaging or non-imaging detector. In one embodiment, the medium can be divided into equal portions (e.g., about 100, 250, 500, or 1000 $\mu m^2$ or more) corresponding to the dimension of the excitation beam and the microscope stage can be stepped in increments such that each portion is placed under the objective for interrogation. In another embodiment, the medium can be observed on a large scale (e.g., the entire plate or a large fraction thereof (e.g., halves, thirds, quarters, tenths, or less) for colonies. In either embodiment, the location of colonies can be determined based on a map created from the scan of the medium. In one embodiment, the microscope stage can be programmed to move to each detected colony in turn to obtain an IF spectrum of each colony. In one embodiment, the manual or automatic scanning can be repeated at regular intervals (e.g., every 0.5, 1, 2, 3, 4, 5, 6, 8, 10, or 12 hours or more) to monitor the appearance and/or growth of colonies. In one embodiment of the invention, the medium is scanned using visible light to detect colonies, e.g., colonies that are large enough to be seen under a microscope. In another embodiment, the medium is illuminated such that an intrinsic property of the colonies (e.g., IF) is detected. Peaks of IF over the background level of the medium indicates the presence of colonies. For example, a fluorescence map of the medium can be constructed, e.g., by using a scanning excitation beam (such as a laser) and a simple, non-imaging detector. In another embodiment, large area imaging using an image capture/acquisition device (e.g., a camera or scanner such as a CCD linear array scanner, a CCD line-scan camera, a CCD 2D array camera, a laser scanning camera, or other device) can be used as described in WO 03/022999 and U.S. Pat. Nos. 5,912,115, 6,153,400, and 6,251,624.

In certain embodiments of the invention, the detection methods can also be used to detect the presence of a microorganism(s) in a sample, with or without identification of the detected microorganism. In some embodiments, the detection methods can be used to monitor samples for contamination by a microorganism, e.g., foodstuffs, pharmaceuticals, drinking water, etc. In one embodiment, the methods can be carried out in a repetitive fashion for constant monitoring for contamination, e.g., once a month, once a week, once a day, once an hour, or any other time pattern. In another embodiment, samples can be tested as needed, e.g., when contamination is suspected or absence of contamination needs to be confirmed. In further embodiments, the detection methods can be used to look for the presence of a microorganism in a clinical sample, e.g., from a wound or blood culture. For example, a sample can be removed from a blood culture at certain time points and the detection method carried out on the sample to determine if the blood culture is positive. In one embodiment, a sample may be taken at a set time point after inoculation of the culture, e.g., 24 hours after inoculation, to determine if the blood culture is positive. In another embodiment, samples can be taken from the blood culture regularly, e.g., every 12, 6, 4, 2, 1, or 0.5 hours, to identify positive blood cultures within a short time of being detectably positive. In certain embodiments of the detection methods, the detection step can optionally be followed by identification/characterization methods as described herein. In other embodiments, the detection methods are partially or fully automated, particularly for the embodiments involving repetitive monitoring of samples.

In certain embodiments, the methods of the invention can be carried out with animal or plant cells instead of microorganisms. In particular, animal cells (e.g., mammalian, avian, insect, cells) or plant cells that can grow in colonies, clumps, or other three-dimensional structures or that are grown on three-dimensional substrates can be detected, monitored, characterized, and/or identified using the techniques disclosed herein. Examples of suitable cells that grow in three-dimensional colonies include, without limitation, stem cells, fibroblasts, and neoplastic cells.

The present invention is further detailed in the following examples, which are offered by way of illustration and is not intended to limit the invention in any manner. Standard techniques well known in the art or the techniques specifically described below are utilized.

EXAMPLES

Example 1

Obtaining Spectra from Colonies on Plates and Membranes

Tests were conducted to determine whether useful spectra could be obtained of colonies directly on blood agar plates (BAP; tryptic soy agar with 5% sheep blood), with and without black membranes (Table 1). Colonies of *E. coli* (EC), *S. aureus* (SA), *E. faecalis* (EF), and *P. aeruginosa* (PA) were grown as indicated in Table 2 and spectra were taken through the UV microscope (10× Objective) coupled with a fiber optic adaptor to a Fluorolog3 spectrometer (Horiba Jobin Yvon, Edison N.J.) and a PMT detector. The EEM was acquired through a wavelength range of Excitation (Ex)=260-550 nm, and Emission (Em)=280-600 nm, every 5 nm with a slit width=5 nm. Where indicated, the interrogation area was narrowed by placing a 1 mm pinhole in the emission path which resulted in an observed area of approximately 0.1 mm. Without the pinhole, the excitation and emission circles as projected on the colonies were equal at approximately 1 mm diameter. The samples that were included in each test run are indicated in Table 2.

TABLE 1

| Test Run | A1 | A2 | A3 | A4 | B1 | B2 |
|---|---|---|---|---|---|---|
| Approx Colony Diameter (mm) | 0.4 | Blank | 0.2-0.35 | 1.0-3.0 | 1.0-3.0 | 1.0-3.0 |
| Membrane | Pall | All | WME | None | None | WME |
| EM Beam Diameter (mm) | 0.1 | 0.1 | 0.1 | 0.1 | 1.0 | 1.0 |
| Integration Time (sec) | 1 | 0.5 | 0.5 | 0.5 | 0.1 | 0.1 |

Membranes:
None = Sheep Blood Agar (SBA)
Pall = Pall Metricel Black gridded Polyethersulfone membrane on SBA
WPC = Whatman Track-Etched Polycarbonate Black membrane on SBA
WME = Whatman Black Mixed Ester membrane on SBA

TABLE 2

| | |
|---|---|
| A1 | EC1 = ATCC 25922 25 hr @ Ambient Temperature (AT) on Pall Metricel Black gridded polyethersulfone membrane on SBA plate. Approximate whole colony diameter spanned ~3 grid dots, the pinhole covered approximately ¼-⅕ of the colony diameter, and 1/20 of the colony area. |
| A2 | Plain BAP and each membrane on BAP |
| A3 | EC3 = ATCC 25922 overnight (O/N) @ Ambient Temperature (AT) + 4 h @ 36° C. to produce a 350 micron diameter colony on WME membrane<br>SA1 = ATCC 25923 O/N @ RT + 4 h @ 36° C. to produce a 200 micron diameter colony on WME membrane |
| A4 | EC2 = ATCC 25922 O/N colony @ 36° C. on BAP<br>SA2 = ATCC 25923 O/N colony @ 36° C. on BAP<br>EF1 = ATCC 29212 O/N colony @ 36° C. on BAP<br>PA1 = ATCC 27853 O/N colony @ 36 C on BAP |
| B1 | EC1 = ATCC 25922 O/N colony @ 36° C. on BAP, colony = 2.3 mm dia<br>EC2 = ATCC 25922 O/N colony @ 36° C., colony = 2.3 mm dia, Slit width = 3 nm<br>SA1 = ATCC 25923 O/N colony @ 36° C. on BAP, colony = 2.0 mm dia<br>EF1 = ATCC 29212 O/N colony @ 36° C. on BAP, colony = 1.2 mm dia<br>PA1 = ATCC 27853 O/N colony @ 36° C. on BAP, colony = 3.0 mm dia |
| B2 | EC1 = ATCC 25922 O/N colony @ 36° C. on WME membrane on SBA, colony dia = 2.0 mm<br>EC2 = ATCC 25922 O/N colony @ 36° C. on WME membrane on SBA, colony dia = 1.6 mm<br>SA1 = ATCC 25923 O/N colony @ 36° C. on WME membrane on SBA, colony dia = 1.2 mm<br>SA2 = ATCC 25923 O/N colony @ 36° C., colony dia = 1.2 mm, Int. Time = 0.05 sec, Slits = 2.5 nm<br>SA3 = ATCC 25923 O/N colony @ 36° C., colony dia = 1.2 mm, Int. Time = 0.1 sec, Slits = 3.0 nm<br>SA4 = ATCC 25923 O/N colony @ 36° C. on WME membrane on SBA, colony dia = 1.1 mm<br>SA5 = ATCC 25923 O/N colony @ 36° C. on WME membrane on SBA, colony dia = 1.2 mm<br>EF1 = ATCC 29212 O/N colony @ 36° C. on WME membrane on SBA, colony dia = 1.0 mm<br>PA1 = ATCC 27853 O/N colony @ 36° C. on WME membrane on SBA, colony dia = 1.1 mm |

Spectra from test run A2 of uninoculated plates are shown in FIGS. 1A-1D. The vertical axis on each figure indicates the Ex range, and the horizontal axis shows the Em range. Spectra were obtained from BAP (FIG. 1A), Pall membrane (FIG. 1B), WME membrane (FIG. 1C), and WPC membrane (FIG. 1D) without microorganisms. The first observation was the difference in background fluorescence between the Pall and Whatman membranes and the BAP. Surprisingly, the black Pall membrane fluoresced strongly in the areas of the spectrum previously found to be important for classification of microbial suspensions, much more so than the unmasked BAP. However, the WME membrane gave the least background fluorescence of all.

Figure 2A:
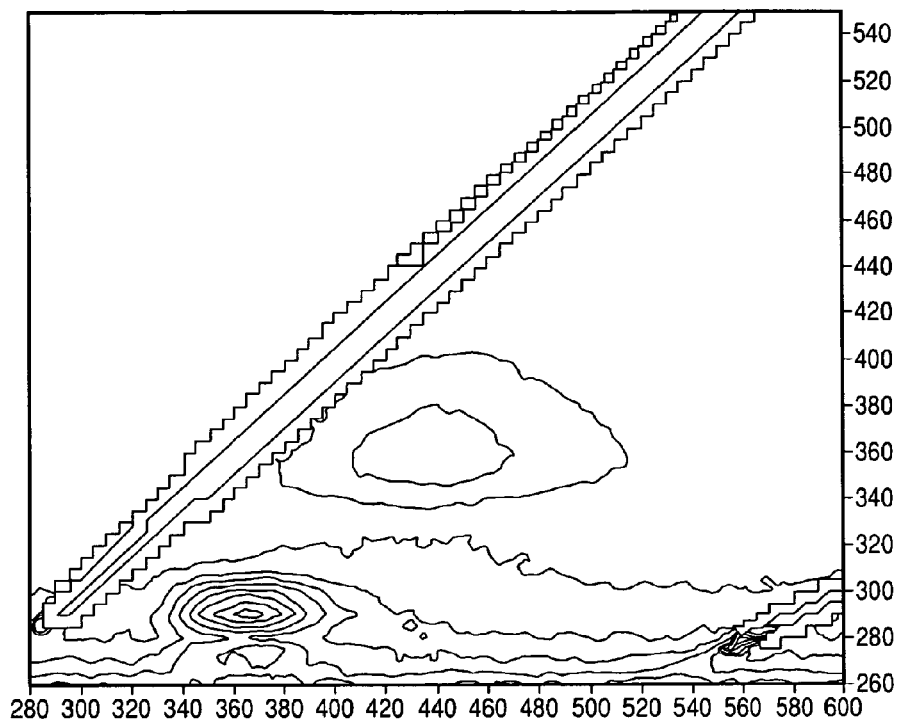
FIGS. 2A-2C show spectra from colonies on WME membrane over BAP obtained from EC3 (A) and SA1 (B), and the results of subtracting the EC3 spectrum from the SA1 spectrum (C).
Figure 2B:
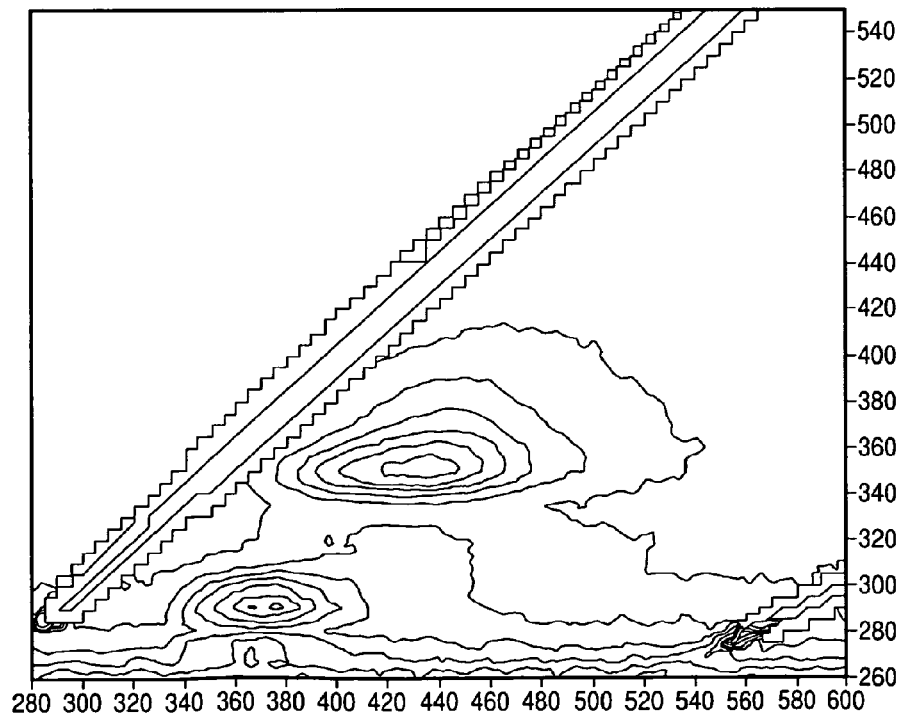
Figure 2C:
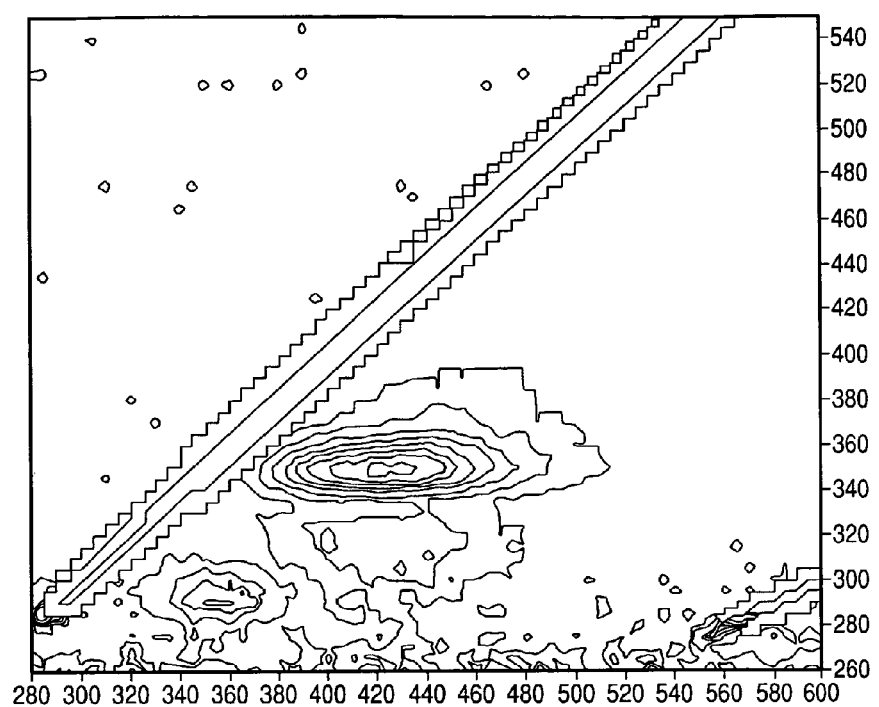

Spectra from test run A3 of colonies on WME membrane over BAP are shown in FIGS. 2A-2C. Spectra were obtained from EC3 (FIG. 2A) and SA1 (FIG. 2B), and the result of subtracting the EC3 spectrum from the SA1 spectrum is shown in FIG. 2C. The spectra of the colonies show clear differences between *S. aureus* and *E. coli*. The fact that some parts of the spectrum are higher for *E. coli* and others are higher for *S. aureus* shows that the differences are present in the overall pattern, and not simply differences in the scale of intensity.

Figure 3A:
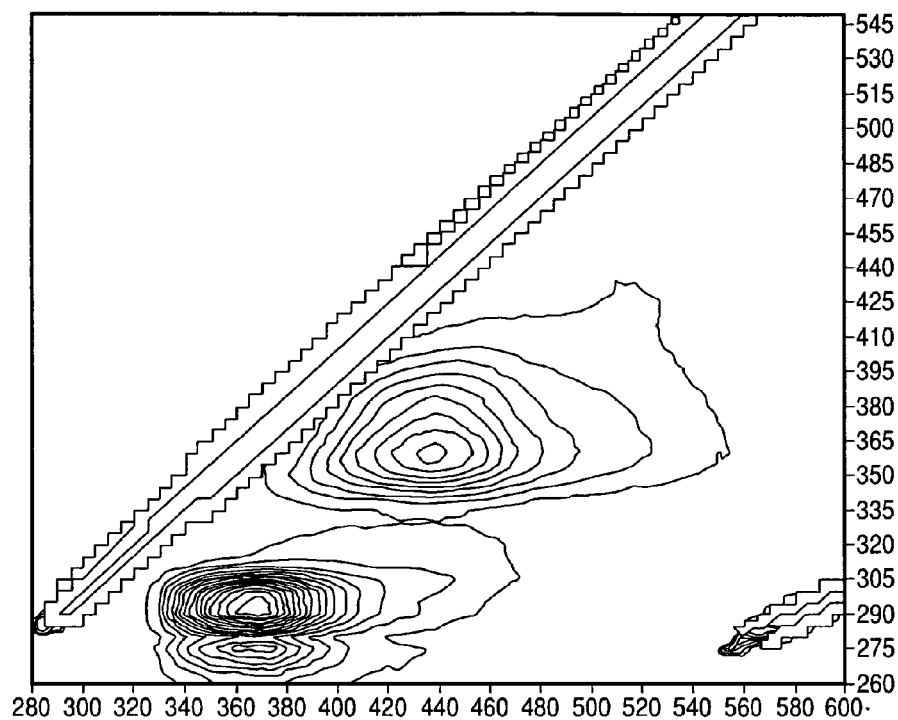
FIGS. 3A-3D show spectra from colonies on BAP without a membrane obtained from EC1 (A), SA1 (B), EF1 (C), and PA1 (D).
Figure 3B:
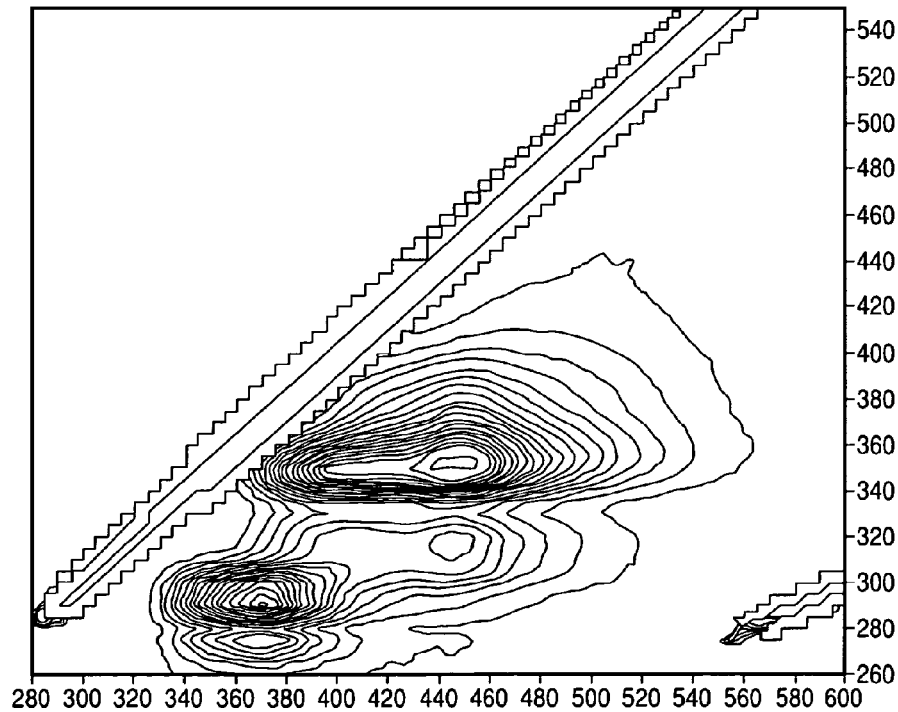
Figure 3C:
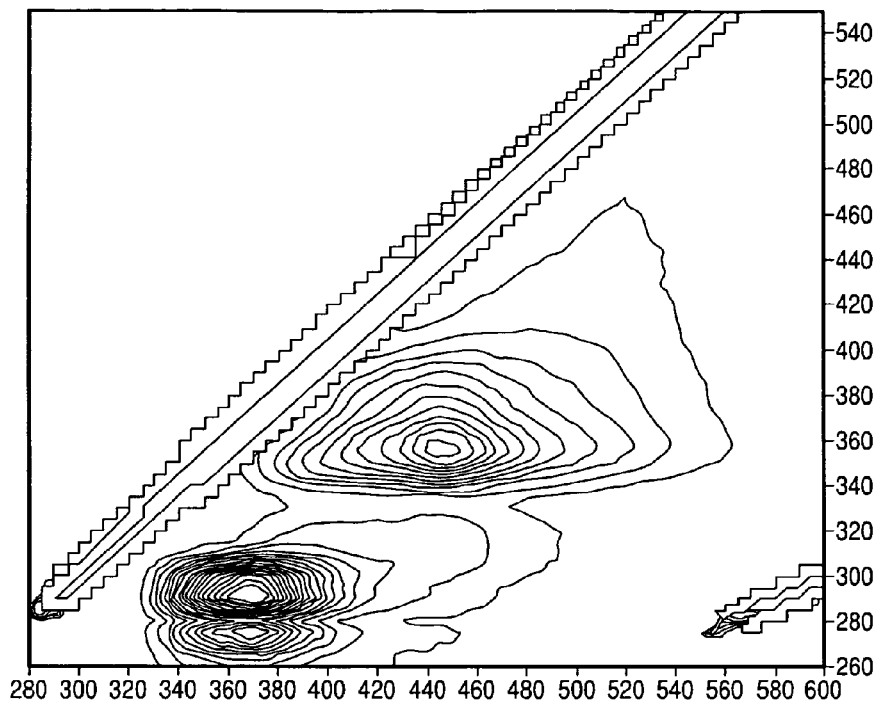
Figure 3D:
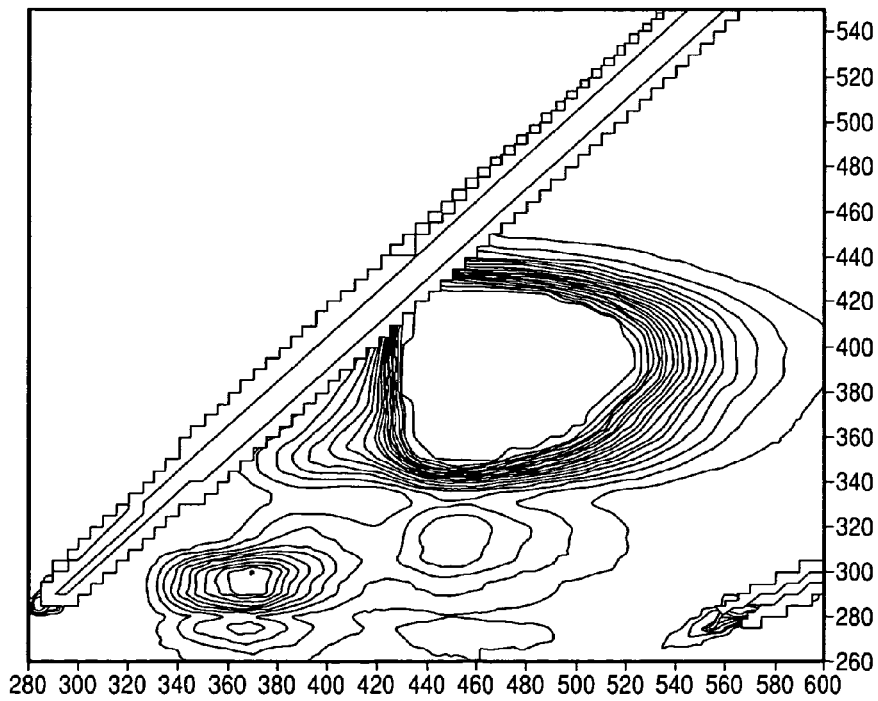

Spectra from test run B1 of colonies on BAP without a membrane are shown in FIGS. 3A-3D. Spectra were obtained from EC1 (FIG. 3A), SA1 (FIG. 3B), EF1 (FIG. 3C), and PA1 (FIG. 3D). Although the different measurement parameters produce much higher intensities than the A3 spectra, and in spite of being measured directly on a BAP without a black membrane, the relative patterns are still similar for the respective species of bacteria.

These experiments showed that intrinsic fluorescence spectra could be obtained of colonies through the microscope directly on a BAP, with or without the aid of a black membrane to reduce background fluorescence, and the patterns observed were characteristic for different types of microorganisms.

Example 2

Scanning for Microcolonies Through the Microscope

Tests were carried out to determine whether colonies growing under the microscope on a motorized stage could be located by using point-by-point IF measurements, and have IF spectra automatically collected of each colony detected. A UV microscope was coupled to a Fluorolog3 (Horiba Jobin Yvon, Edison N.J.) spectrometer, which served as the fluorescence excitation source and the emission measurement device, via fiber optic cables. The microscope's motorized stage was fitted with a compact plate incubator constructed with coils of tubing fed by a circulating waterbath set to 36° C. The incubator was also equipped with a UV transparent window made from a quartz coverslip. Various agar media were inoculated by spread method with *E. coli* ATCC 25922 (EC) and/or *S. aureus* ATCC 25923 (SA) as indicated in Table 3. Some runs used a light blocking material, either a black Whatman Mixed Ester (WME) membrane or charcoal, to reduce the fluorescence coming from the media itself.

After inoculation, the microscope's motorized stage was programmed to periodically move across the agar plate in a search grid and measure the fluorescence at each point with one or more excitation/emission wavelength pairs. The Fluorolog3 was programmed with slit widths set to 10 nm and integration times set to 500 ms (test runs A-E) or 1000 ms (test runs F-H). The excitation beam projected on the surface of the agar was restricted to roughly 0.1 mm diameter by placing a pinhole in the excitation beam within the microscope. Corresponding with this beam size, the microscope stage was stepped in 0.1 mm increments so that 10 steps covered 1 mm of distance. The emission beam was not restricted with a pinhole, but the microscope was shrouded during measurements to prevent any stray light that was not generated by the excitation beam from being detected.

For test runs G and H, an algorithm was developed to automatically calculate the location of growing colonies. For Run H the program was further enhanced so that all colonies that were detected triggered the microscope stage to move to their locations in sequence and collect their IF spectra. The spectra collected were a subset of a full matrix scan that comprised 300 EEM points selected to reduce the acquisition time required. Also for the sake of time, the instrument was programmed to take spectra of no more than 10 colonies.

TABLE 3

Variables for each experimental run

| Run | Bacteria | Search Wavelengths | Area Steps | Scan Time | Media |
|---|---|---|---|---|---|
| A | EC | 305-365 & 440-525 | 59 × 60 | 87 min | WME-SBA |
| B | EC | 305-365 & 440-525 | 68 × 68 | 115 min | WME-SBA |
| C | EC | 305-365 | 71 × 71 | 125 min | TSA w/ 2% Charcoal |
| D | EC | 440-525 | 100 × 100 | 122 min | TSA w/ 2% Charcoal |
| E | EC | 305-365 | 97 × 97 | 115 min | SBA |
| F | EC & SA | 440-525 | 72 × 73 | 111 min | SBA |
| G | EC & SA | 305-365 | 61 × 61 | 46 min | SBA |
| H | EC & SA | 440-525 | 70 × 70 | 61 min | SBA |

Run A had an instrument problem that stopped the program after 6 h, and no colonies were detected during that time.

Run B showed one colony barely above background fluorescence at 8 h, 2 clearly visible at 10 h, and 3 at 12 h and later. The difference between the colony signals and the background was larger at 440-525 nm (roughly 4× background) than at 305-365 nm (roughly 2× background).

Run C had no colonies within the scan area due to a low inoculum.

Run D showed 1 colony at 8 h, and 3 at 10 h and later.

Run E had no colonies in the field of view initially. One colony grew into the field edges by 12 h, 3 at 14 h and later.

Figure 4A:
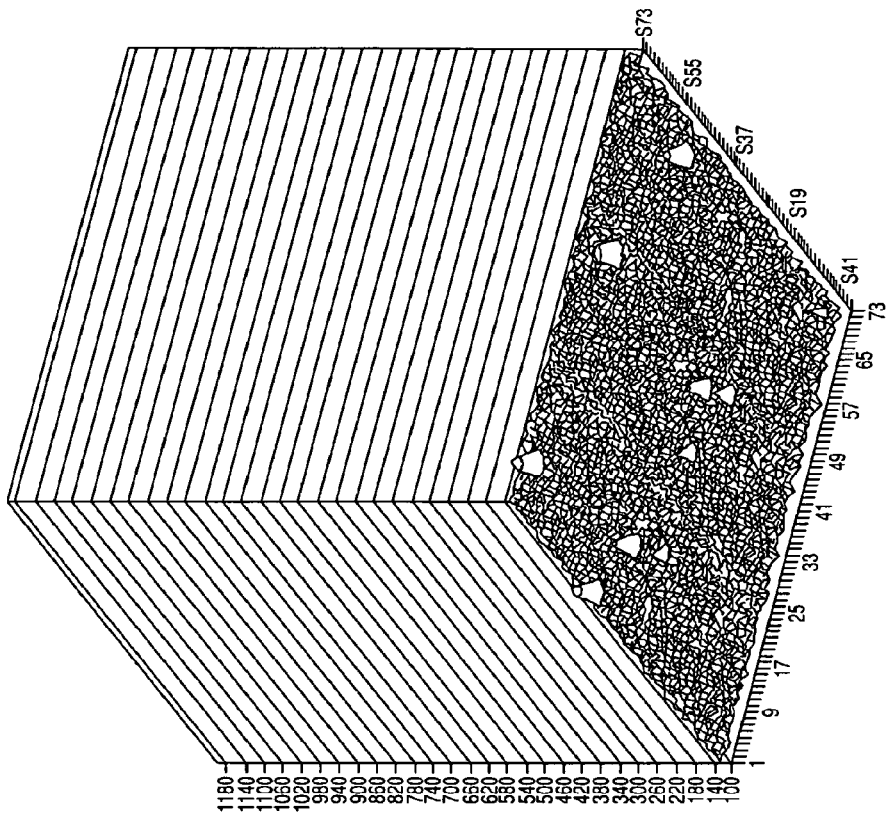
Figure 4B:
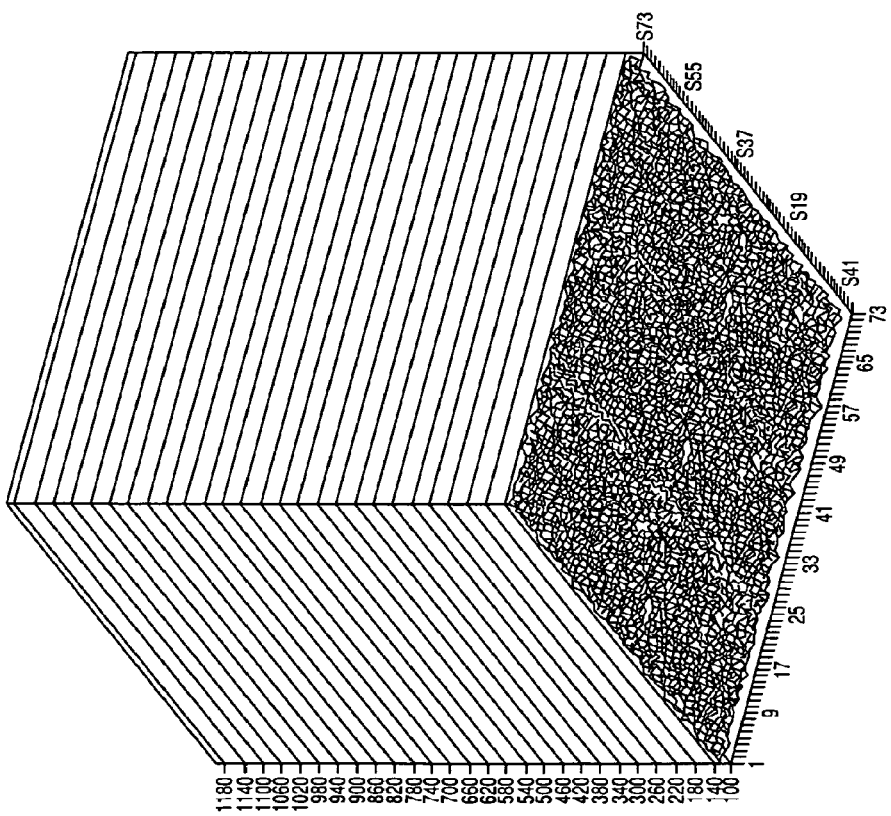
Figure 4C:
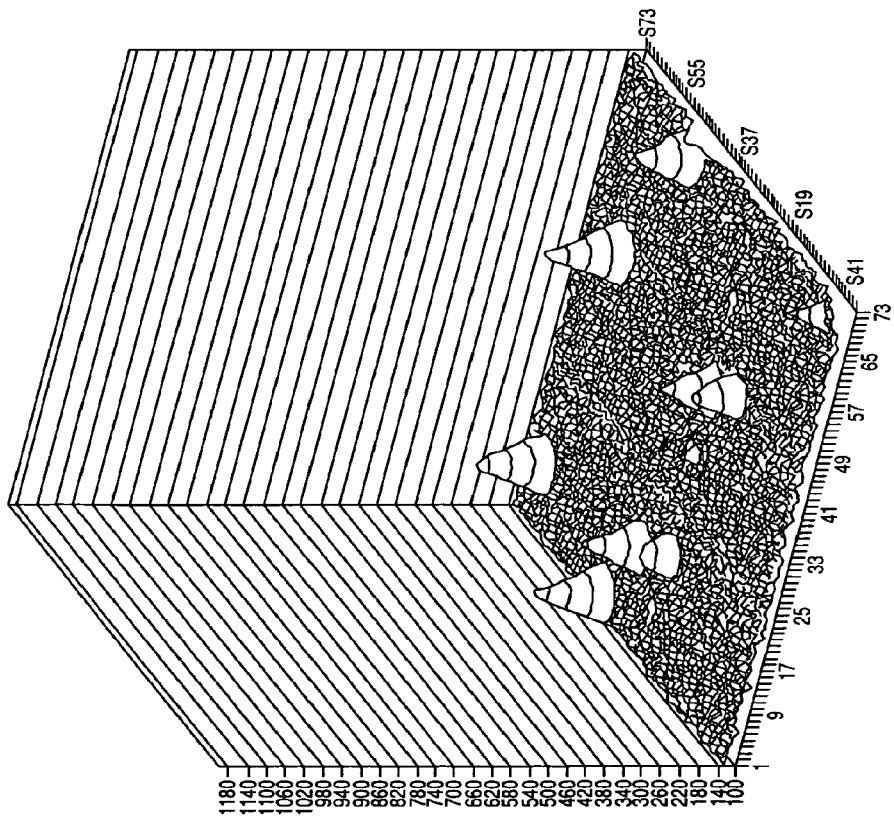
Figure 4D:
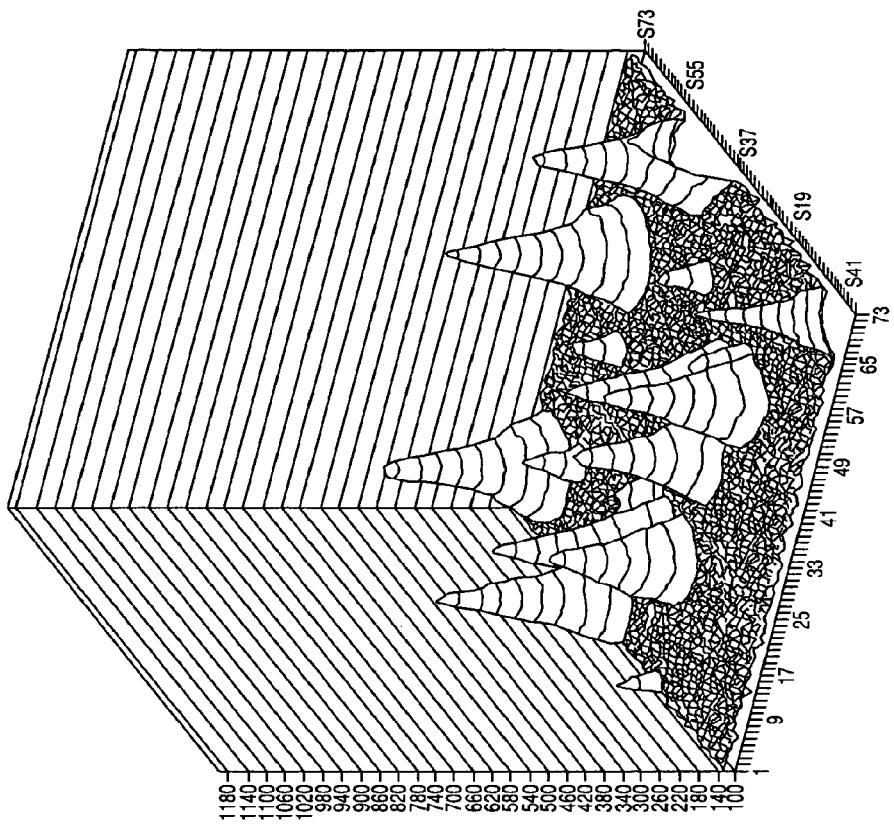
Figure 5A:
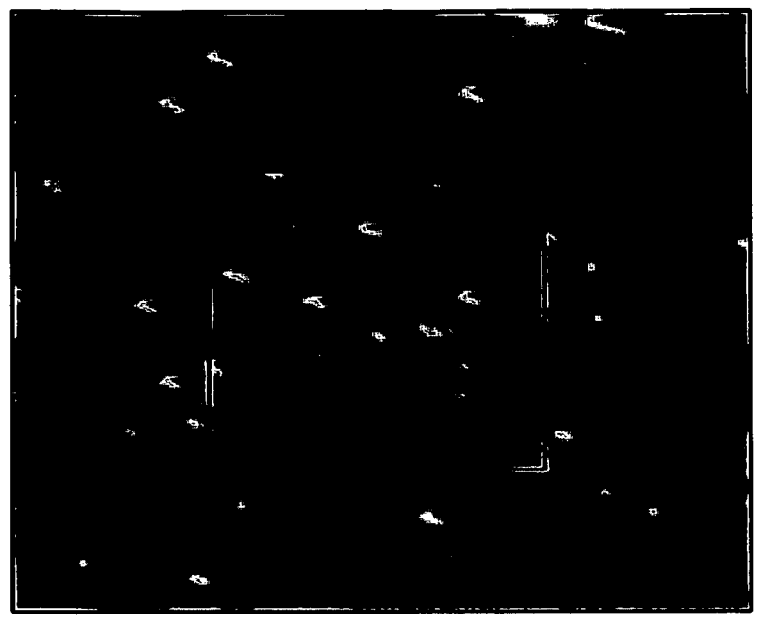
FIGS. 5A-5B show a close-up image of the BAP from run F after 24 h (A), and a contour plot of fluorescence intensity from the search scan at 12 h showing corresponding colony locations (B).
Figure 5B:
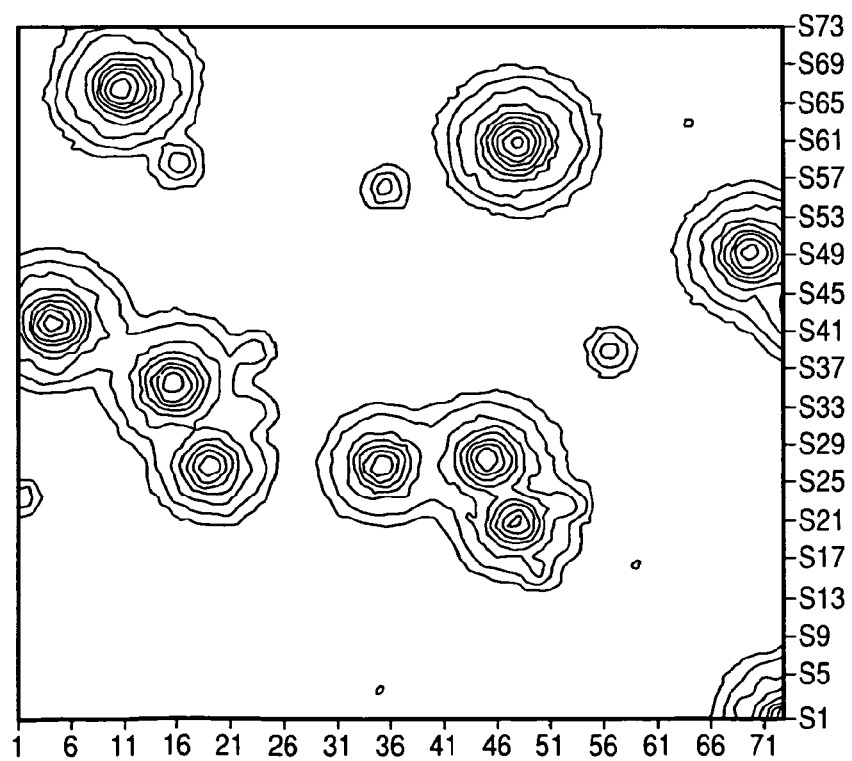

Run F with a mixed inoculum showed 10 colonies determined to be EC by 8 h, additionally 3 SA by 10 h, and 2 more SA at times greater than 12 h. Three dimensional plots of the point-by-point IF search scans of run F are shown in FIGS. 5A-5F, where height equals fluorescence intensity. The plots show measurements taken at 6 h where the first detected colony was observed (FIG. 4A), 8 h (FIG. 4B), 10 h (FIG. 4C), 12 h (FIG. 4D), 16 h (FIG. 4E), and 24 h (FIG. 4F). Note that all colonies visible at 8 h were *E. coli*, whereas the additional colonies seen at 10 h and later were *S. aureus*. A close-up image of the BAP from run F after 24 h is shown in FIG. 5A with the search scan area outlined, A contour plot of fluorescence intensity from the search scan at 12 h showing corresponding colony locations is shown in FIG. 5B.

Run G showed 1 EC colony at 8 h and 2 EC colonies at 9 h. An instrument error halted acquisition at 10 h and 12 h, but when restarted at 12 h there were 5 colonies detected; 2 EC and 3 SA. The colony detection algorithm successfully identified the location of all 5 colonies.

Run H had condensation on the observation window that interfered with all scans prior to 9 h, at which time 3 EC colonies were detected and spectra taken. The same 3 EC were detected on subsequent scans, and, beginning at 13 h, 4 SA colonies were also detected and spectra taken.

The experimental results show that intrinsic fluorescence can be used to detect the presence and number of microorganism microcolonies while they are growing directly on agar plates, whether or not a background blocking membrane or charcoal are used. Furthermore, once located, it is relatively simple to take full spectra of the microcolonies in situ for classification.

Example 3

Classification of Microorganism Colonies on Agar Plates

Tests were carried out to determine whether microbial colonies could be classified from IF spectra taken directly on the agar plate where they were grown.

The spectral acquisition was done across an excitation (Ex) and emission (Em) matrix of wavelengths 260-580 nm and 260-680 nm, respectively, in a subset of 300 EEM points selected to reduce the acquisition time required. Additionally, all reflectance wavelengths (where Ex=Em) were also read. For fluorescence, the slit widths were set to 5 nm bandpass and the integration time was 1000 ms. Each 300 point acquisition took approximately 8.1 min to complete.

Table 4 lists the microorganisms tested, which comprised 6 isolates each of 20 species for a total of 120 tests. Where used to indicate groupings other than by species, the term Clinical Gram (ClinGram) refers to the classification level possible by a highly skilled observer reading a Gram stain, not just positive, negative or yeast (Table 5). For example, Staphylococci are Gram positive cocci in clusters, while many Streptococci are Gram positive cocci in chains.

TABLE 4

| Gram Negative | Gram Positive | Yeast |
|---|---|---|
| A. baumanii, 6 isolates | S. aureus, 6 isolates | C. tropicalis, 6 isolates |
| E. aerogenes, 6 isolates | S. epidermidis, 6 isolates | C. glabrata, 6 isolates |
| E. cloacae, 6 isolates | S. pneumoniae, 6 isolates | C. albicans, 6 isolates |
| E. coli, 6 isolates | E. faecium, 6 isolates | |
| K. pneumoniae, 6 isolates | E. faecalis, 6 isolates | |
| P. aeruginosa, 6 isolates | S. pyogenes, 6 isolates | |
| S. maltophilia, 6 isolates | S. agalactiae, 6 isolates | |
| S. marcescens, 6 isolates | B. subtilis, 6 isolates | |
| | B. cereus, 6 isolates | |

Table 5 shows the results of classification modeling by Forward Stepwise Linear Discriminant Analysis with "Leave-one-out" cross-validation. "Leave-one-out" cross-validation was chosen because it efficiently makes use of small data sets, estimating the results as if a number of "unknowns" were tested equal to the "training" set, without needing to run twice as many tests. In the tables, the "Number of DA steps" refers to the number of Discriminant Analysis steps completed, which may or may not be the actual number of EEM points used to produce the indicated results. Typically the step number is equal to the number of ExEm points in the model, but sometimes the number of model points is less if points were removed, rather than added, during some steps.

Since Discriminant Analysis can "find" false correlations in the random fluctuations within the data, given a sufficient number of sufficiently "noisy" data points, cross validation is essential to estimate the true success of a given classification model. Generally, the non-cross-validated results will trend to 100% correct with increasing step count, while the cross-validated results will rise to a peak, and then tail back down. The model with the number of steps near the cross-validation peak can be considered optimized for a given data set. Table 5 shows the results of each classification model run, both with and without cross validation, at the point where the cross validated results are optimized.

The classification for each microorganism by discriminant analysis was considered to be correct if the model's first choice for classification was the actual identity of the microorganism, regardless of how close the other choices may have been. Also shown is the is number and percentage of microorganisms for which the actual identity is within the top 3 choices of the model's classification, indicating a good predictive, if as yet imperfect, model for classification.

The spectra from colonies clearly show the potential to classify microorganisms. There is probably some noise in the data, as indicated by the fact that the results are improved by binning 2 adjacent ExEm points. Two known factors contributing to the noisy data come from inconsistent positioning of the measurement beam on the colonies, and the low light levels reaching the detector through the apparatus. For this study, positioning the excitation beam on the center of the colonies with the microscope camera was difficult because the lighting available for visualization was not optimal. In fact, the positioning was observed to be off on some occasions, which was corrected, but it is likely that other mispositionings went unnoticed. Noise in the fluorescence signal itself was also large because the amount of fluorescent energy reaching the detectors was more than 1000 times lower than for suspensions of microorganisms. This was because of the fiber optic and microscope configuration, which is a flexible research tool but is not optimized for this type of measurement. An optical system designed for this task could easily overcome this issue.

TABLE 5

| Classification Grouping | Number of DA Steps | Number (%) Correct w/o Cross Validation | | Number (%) Correct with Cross Validation | | Number (%) Within Top3 with Cross Validation | | EEM Points Binned |
|---|---|---|---|---|---|---|---|---|
| Species | 30 | 118 | 98.3% | 86 | 71.7% | 108 | 90.0% | 1 |
| Species | 18 | 113 | 94.2% | 94 | 78.3% | 114 | 95.0% | 2 |
| ClinGram | 18 | 118 | 98.3% | 112 | 93.3% | 118 | 98.3% | 2 |

Example 4

Improved Classification of Colonies with Less Noise

Tests were conducted to determine whether better positioning and increased light throughput could improve the classification of microbial colonies with intrinsic fluorescence. The experiment of Example 3 was repeated with the same equipment and the same microorganism strains, but with a modified method. The spectral acquisition was done across the same Excitation (Ex) and Emission (Em) wavelength range (Ex=260-580 nm, Em=260-680 nm) but with a different subset of 312 wavelengths that cover the same key areas of the spectrum, but is more conducive to binning of values than was the previous subset. The main reason for using subsets is to reduce the time required to collect spectra with the current equipment. The monochromator slit widths were widened to 7 nm bandpass over the previous 5 nm, which increased the measured fluorescence by roughly 2-fold. The integration time was kept at 1000 ms, and each acquisition took approximately 9.8 min to complete.

Table 6 shows the results of classification modeling by Forward Stepwise Linear Discriminant Analysis with "Leave-one-out" cross-validation. As before, the classification was considered correct if the model's first choice for classification was the actual identity of the microorganism, regardless of how close the other choices may have been. Classification performance to the species level is shown based on individual data points (no binning), binning 3 adjacent fluorescence readings in an "L" pattern on the ExEm matrix, and binning of 4 adjacent EEM points in a square. Also, classification to the Clinical Gram level is shown with "3L" binning.

The method changes to improve the consistency of the fluorescence readings combined with the increased light throughput substantially improved the classification success. Of the main improvements, better positioning probably contributed more to the performance gain than the increased light throughput, and it is likely that fluorescence readings from more than one location in each colony could be used to further enhance classification accuracy. Limitations in the current equipment permitted only a modest 2-fold increase in signal without reducing spectral resolution or increasing the scan time substantially, and it is evident that there is still significant read noise in the fluorescence spectra.

The read noise is partially overcome by binning adjacent points, which has no positive effect on other factors affecting classification success, but reduces the spectral resolution accordingly. That binning helps also indicates that some spectral resolution might be sacrificed to improve read noise in an optimized system. The improvement with binning, however, was not as large as the difference between these data and the results of the previous method, which probably shows that positioning of the measurement played a larger role. Further improvements in classification success could be made with automated positioning and optimized optics as would be well within the skill of the ordinary artisan.

The foregoing is illustrative of the present invention, and is not to be construed as limiting thereof. The invention is defined by the following claims, with equivalents of the claims to be included therein. All publications, patent applications, patents, patent publications, and any other references cited herein are incorporated by reference in their entireties for the teachings relevant to the sentence and/or paragraph in which the reference is presented.

TABLE 6

| Classification Grouping | Number of DA Steps | Number (%) Correct w/o Cross Validation | | Number (%) Correct with Cross Validation | | Number (%) Within Top3 with Cross Validation | | EEM Points Binned |
| --- | --- | --- | --- | --- | --- | --- | --- | --- |
| Species | 28 | 120 | 100% | 105 | 87.5% | 116 | 96.7% | 1 |
| Species | 40 | 120 | 100% | 109 | 90.8% | 113 | 94.2% | 3 |
| Species | 40 | 120 | 100% | 107 | 89.2% | 117 | 97.5% | 4 |
| ClinGram | 28 | 120 | 100% | 119 | 99.2% | 120 | 100.0% | 3 |

That which is claimed is:

1. A method of detecting and characterizing a microorganism on a solid or semi-solid medium, comprising:
   (a) scanning a solid or semi-solid medium, known to contain, or that may contain one or more microorganism colonies to locate any colonies present on the medium;
   (b) interrogating one or more of said colonies located during step (a) with an excitation beam that is smaller in diameter than the colony to be interrogated, to produce intrinsic fluorescence (IF) measurements characteristic of a microorganism in said colony; and
   (c) characterizing the microorganism in the colony based on said intrinsic fluorescence (IF) measurements, wherein said microorganism is characterized into one or more classification models selected from the group consisting of Gram Groups, Clinical Gram Groups, Therapeutic Groups, Functional Groups, and Natural Intrinsic Fluorescence Groups.

2. The method of claim 1, wherein said scanning comprises a point-by-point scanning of the surface of said solid or semi-solid medium.

3. The method of claim 1, wherein said colony is a microcolony having a diameter of less than 50 μm.

4. The method of claim 1, wherein said interrogation step is non-invasive.

5. The method of claim 1, wherein said IF measurements are produced by spectroscopy and said spectroscopy comprises determining an excitation-emission matrix (EEM).

6. The method of claim 5, wherein said EEM comprises at least two different wavelength pairs.

7. The method of claim 5, wherein said EEM is compared to a database of EEMs of known microorganisms.

8. The method of claim 1, further comprising addition of an identifier agent to the medium or sample and wherein the characterization is based in part on the presence and/or amount of said identifier agent in the colony or in microorganisms recovered from the colony.

9. The method of claim 8, wherein said identifier agent is an affinity ligand, antibody or fragment thereof, nucleic acid probe, antibiotic, aptamer, peptide mimetic, phage-derived binding protein, lectin, host defense peptide, bacteriocin, bacteriophage, dye, or any combination thereof.

10. The method of claim 1, wherein said solid or semi-solid medium comprises one or more nutrients useful for the growth of said microorganism and one or more additives, wherein said one or more additives enhance said intrinsic fluorescence measurements of said microorganism colonies on said solid or semi-solid medium.

11. The method of claim 10, wherein said one or more additives are selected from the group consisting of protein hydrolysates, amino acids, meat and vegetable extracts, carbohydrate sources, buffering agents, resuscitating agents, growth factors, enzyme cofactors, mineral salts, metal supplements, reducing compounds, chelating agents, photosensitizing agents, quenching agents, reducing agents, oxidizing agents, detergents, surfactants, disinfectants, selective agents and metabolic inhibitors.

12. The method of claim 1, wherein interrogating a colony comprises measuring epifluorescence.

13. The method of claim 1, wherein interrogating a colony comprises measuring reflected light.

* * * * *